United States Patent [19]

Koestner et al.

[11] Patent Number: 5,300,093

[45] Date of Patent: Apr. 5, 1994

[54] APPARATUS AND METHOD FOR MEASURING, FORMATTING AND TRANSMITTING COMBINED INTRACARDIAC IMPEDANCE DATA AND ELECTROGRAMS

[75] Inventors: Ken Koestner, Englewood; Bruce M. Steinhaus, Parker; Randy T. Wells, Littleton, all of Colo.

[73] Assignee: Telectronics Pacing Systems, Inc., Englewood, Colo.

[21] Appl. No.: 944,466

[22] Filed: Sep. 14, 1992

[51] Int. Cl.⁵ ............................................. A61N 1/37
[52] U.S. Cl. .................................................... 607/32
[58] Field of Search ................... 128/419 PG, 419 PT, 128/697, 734

[56] References Cited

U.S. PATENT DOCUMENTS

| | | | |
|---|---|---|---|
| 4,223,678 | 9/1980 | Langer et al. | 128/419 D |
| 4,407,288 | 10/1983 | Langer et al. | 128/419 PG |
| 4,556,063 | 12/1985 | Thompson et al. | 128/419 PT |
| 4,566,456 | 1/1986 | Koning et al. | 128/419 PG |
| 4,688,573 | 8/1987 | Alt | 128/419 PG |
| 4,692,719 | 9/1987 | Whigham | 332/11 D |
| 4,702,253 | 10/1987 | Nappholz et al. | 128/419 PG |
| 4,809,697 | 3/1989 | Causey, III et al. | 128/419 PT |
| 4,901,725 | 10/1990 | Nappholz et al. | 128/419 PG |
| 5,003,976 | 4/1991 | Alt | 128/419 PG |
| 5,058,583 | 10/1991 | Geddes et al. | 128/734 |
| 5,197,467 | 3/1993 | Steinhaus et al. | 128/419 PG |

Primary Examiner—William E. Kamm
Attorney, Agent, or Firm—Gottlieb Rackman & Reisman

[57] ABSTRACT

A patient-implantable cardiac stimulation apparatus adapted to measure body impedance, derive at least one physiological parameter from the impedance measurement, sample a time sequence of the physiological parameter and transmit the sequence to an external monitoring device for display and analysis. The apparatus may also sense intracardiac electrograms while it is measuring body impedance and deriving the physiological parameter, in which case it formats and transmits a combined intracardiac electrogram and physiological signal to the monitoring device.

18 Claims, 14 Drawing Sheets

APPARATUS AND METHOD FOR MEASURING, FORMATTING AND TRANSMITTING COMBINED INTRACARDIAC IMPEDANCE DATA AND ELECTROGRAMS

TECHNICAL FIELD

This invention relates to programmable implanted cardiac stimulation devices such as pacemakers, defibrillators and antitachycardia pacemakers, which sense and measure physiological signals based upon body impedance measurements, format these physiological signals and transmit formatted signals to an external monitoring device by means of telemetric communication.

BACKGROUND OF THE INVENTION

In addition to performing therapeutic operations, conventional implanted cardiac stimulation devices may monitor and transmit cardiac electrical signals (e.g., intracardiac electrograins) to an external diagnostic device to observe electrical activity of a heart. It is common for implanted cardiac stimulation devices to send intracardiac electrogram signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

For example, U.S. Pat. No. 4,223,678, entitled "Arrhythmia Recorder for Use with an Implantable Defibrillator", issued to Langer et al. on Sep. 23, 1980, discloses an arrhythmia record/playback component within an implantable defibrillator. ECG data is converted from analog to digital form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry.

Langer et al. in U.S. Pat. No. 4,407,288, entitled "Implantable Heart Stimulator and Stimulation Method", issued Oct. 4, 1983, discloses a programmable, microprocessor-based implantable defibrillator which senses and loads ECG data into a memory via a direct memory access (DMA) operation. A processor analyzes this ECG data in the memory to detect the occurrence of an arrhythmia event afflicting a patient's heart. Upon such an event, the defibrillator may generate a therapy to terminate the arrhythmia event and store the ECG data sequence, which corresponds to the arrhythmia event, for transmission to an external monitoring device and later study. In normal circumstances, when no arrhythmia event is occurring, the defibrillator continuously overwrites the ECG data in the memory.

U.S. Pat. No. 4,556,063, entitled "Telemetry System for a Medical Device", granted to D. L. Thompson et al. on Dec. 3, 1985, teaches a pulse interval telemetry system which is capable of transmitting analog data, such as sensed intracardiac electrogram signals, without converting analog data to a digital numeric value. The Thompson et al. telemetry system is capable of sequentially transmitting both digital and analog data, individually and serially, in either an analog or a digital format, to a remote receiver.

Causey et al., in U.S. Pat. No. 4,809,697, entitled "Interactive Programming and Diagnostic System for Use with Implantable Pacemaker", issued Mar. 7, 1989, disclose a programmer system for use with implantable programmable pacemakers that offers communications and diagnostic capabilities, including real-time and prospective analysis of the pacemaker operation, as it interacts with the heart. A graphical display is presented which illustrates the source of stimulating pulses in the atrium or the ventricle, the response or lack of response of the heart to such pulses and the existence and duration of refractory periods, for example. This capability is useful for understanding and analyzing the complex operation of dual chamber pacemakers. In particular, the improvement offered by the Causey et al. system over previous programmers is a display capability which includes a programmed time interval screen for illustrating a graphical or tabular representation of the programmed time intervals associated with the operation of an implanted pacemaker, allowing a user to quickly and easily understand and visualize the interaction between the timing of implantable device events and the body functions it monitors or controls.

Recently, cardiac pacemakers have included rate adaptive sensors to determine an appropriate rate for pacing a patient according to metabolic demands of the body. For example, U.S. Pat. No. 4,702,253, entitled "Metabolic-Demand Pacemaker and Method of Using the Same to Determine Minute Volume", granted to T. A. Nappholz et al. on Oct. 27, 1987, discloses a rate-responsive pacemaker which senses impedance in the pleural cavity of a patient and derives respiratory minute volume as a function of the measured impedance. In turn, the respiratory minute volume measurement is correlated with pacing rate, the greater the amount of air exchanged, the greater the need for a higher pacing rate. U.S. Pat. No. 4,901,725, entitled "Minute Volume Rate-Responsive Pacemaker", issued to T. A. Nappholz et al. on Feb. 20, 1990, teaches an improved minute volume rate-responsive pacemaker, which also sets pacing rate according to minute volume measured using an impedance measurement. U.S. Pat. No. 5,197,467, entitled "Multiple Parameter Rate Responsive Cardiac Stimulation Apparatus", issued to B. M. Seinhaus et al. on Mar. 30, 1993, discloses an apparatus which employs multiple physiological rate control parameters, which are analyzed to determine the best pacing rate. The frequency content of the measuring current determines the respective parameter being measured.

One problem with rate responsive pacemakers which employ a sensor to sense a physiological parameter is that, after long term implantation, the time waveform of the sensed signal is not available for visualization, measurement or analysis. There has been no way to monitor changes in the sensed signal over time which may occur as the lead/tissue interface matures. Furthermore, the inability to monitor the sensor signal has led to some confusion concerning what the true physiological basis is for the signal which is sensed. For example, some clinicians have suggested that the respiration measurement for a minute volume rate-responsive pacemaker actually measures patient motion or vibration, rather than respiration. E. Alt, in U.S. Pat. No. 5,003,976, entitled "Cardiac and Pulmonary Analysis via Intracardiac Measurements with a Single Sensor", granted Apr.

2, 1991, compounds this confusion by showing that a single sensor can sense different physiological signals, as well as signals having a non-physiological basis, depending on the application of different filters to the incoming sensed signal stream.

It is desirable, therefore, to have the capability in an implantable cardiac stimulation apparatus to transmit sensed physiological signals to an external monitoring device for display and analysis.

Accordingly, it is a primary object of the present invention to provide an improved apparatus and method for sensing physiological signals based upon a measurement of body impedance, formatting these signals and transmitting the formatted signals to an external monitoring device, such as a pacemaker programmer, for display.

It is a further object of the present invention to provide an improved capability for visualizing physiological signals to identify a physiological basis for the origin of such signals and confirm that impedance signals, thought to respond to respiration, the forces of cardiac contraction and body motion, do actually respond to these sources.

It is a still further object of the present invention to provide an improved capability for the visual monitoring of physiological signals over time to allow observation of changes in such signals in a chronically implanted device.

It is an additional object of the present invention to provide an improved capability to identify noise sources which affect a physiological signal to allow for the design of filters to remove or reduce the influence of noise signals.

It is another object of the present invention to provide, in a long term implanted rate adaptive heart stimulation device, an improved capability to externally monitor physiological signals over time to calibrate the transfer function for mapping the physiological signal characteristics into a stimulation rate.

It is an accessory object of the invention to transmit a physiological signal to an external monitoring apparatus to allow diagnostic testing of a physiological sensor, leads and measuring circuit.

It is a supplementary object of the invention to provide raw data for physiological research, such as research relating to respiratory ambulatory physiology.

It is an important object of the present invention to provide for simultaneous transmission of combined intracardiac electrogram and physiological signals.

It is an object of the present invention to provide for simultaneous transmission of combined intracardiac electrogram and physiological signals to supply information, additional to cardiac electrical signals, regarding placement of leads during implantation.

It is a supplemental object of the present invention to provide for simultaneous display of intracardiac electrogram and respiration signals to supply information allowing the detection of arrhythmia conditions. For example, an increase in minute volume shown in the respiration signal indicates an exercise condition of a patient. An increase in heart rate concurrent with an increase in minute volume measurement indicates that the fast heart rhythm results from exercise rather than a pathological arrhythmia.

It is a still further object of the present invention to provide for a simultaneous display of intracardiac electrograms and mechanical cardiac contraction waveforms, which indicate a measure of cardiac contractility, denoting the ability of the heart to pump in response to propagated, stimulating electrical waves.

Further objects and advantages of the invention will become apparent as the following description proceeds.

SUMMARY OF THE INVENTION

Briefly stated, and in accordance with the principles of the present invention, a patient-implantable cardiac stimulation apparatus, and method of operating such apparatus, are provided to monitor a physiological signal and transmit a representation of this signal to an external monitoring device for display. The cardiac stimulation apparatus includes a sensor, which is adapted to measure internal impedance within the patient's body, and a means for deriving one or more time-varying physiological parameters as a function of the measured impedance signal. The cardiac stimulation apparatus also includes a means for formatting samples of each physiological parameter into a digital time sequence of samples representing the amplitude of the parameter, and a telemetry system which is adapted to transmit the formatted physiological parameter samples to the external monitoring device.

To provide for further hemodynamic and physiologic monitoring, the cardiac stimulation apparatus may also include a means for measuring cardiac electrical signals, a means for digitally sampling the amplitude of these signals to thereby generate a time sequence of intracardiac electrogram samples, and a means for formatting intracardiac electrogram samples and combining the formatted signals with samples of the time-varying physiological parameter so that the telemetry system simultaneously transmits combined intracardiac electrogram and physiological signal samples.

More particularly, the cardiac stimulation apparatus signal formatting and combining means may encode each of the physiological parameter samples into a single serial bit stream of data. Each bit of encoded physiological signal may replace a bit of the transmitted digital intracardiac electrogram signal, thereby truncating the intracardiac electrogram signal. In the case of an embodiment of the apparatus which does truncate the intracardiac electrogram signal, a further refinement of the apparatus may reaccumulate the truncated bits to restore signal fidelity.

In various embodiments of the present invention, the time-varying physiological signals derived from the measured impedance signal may include one or more of the parameters of respiration, mechanical cardiac contraction and patient motion.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

DETAILED DESCRIPTION OF THE INVENTION

Figure 1:
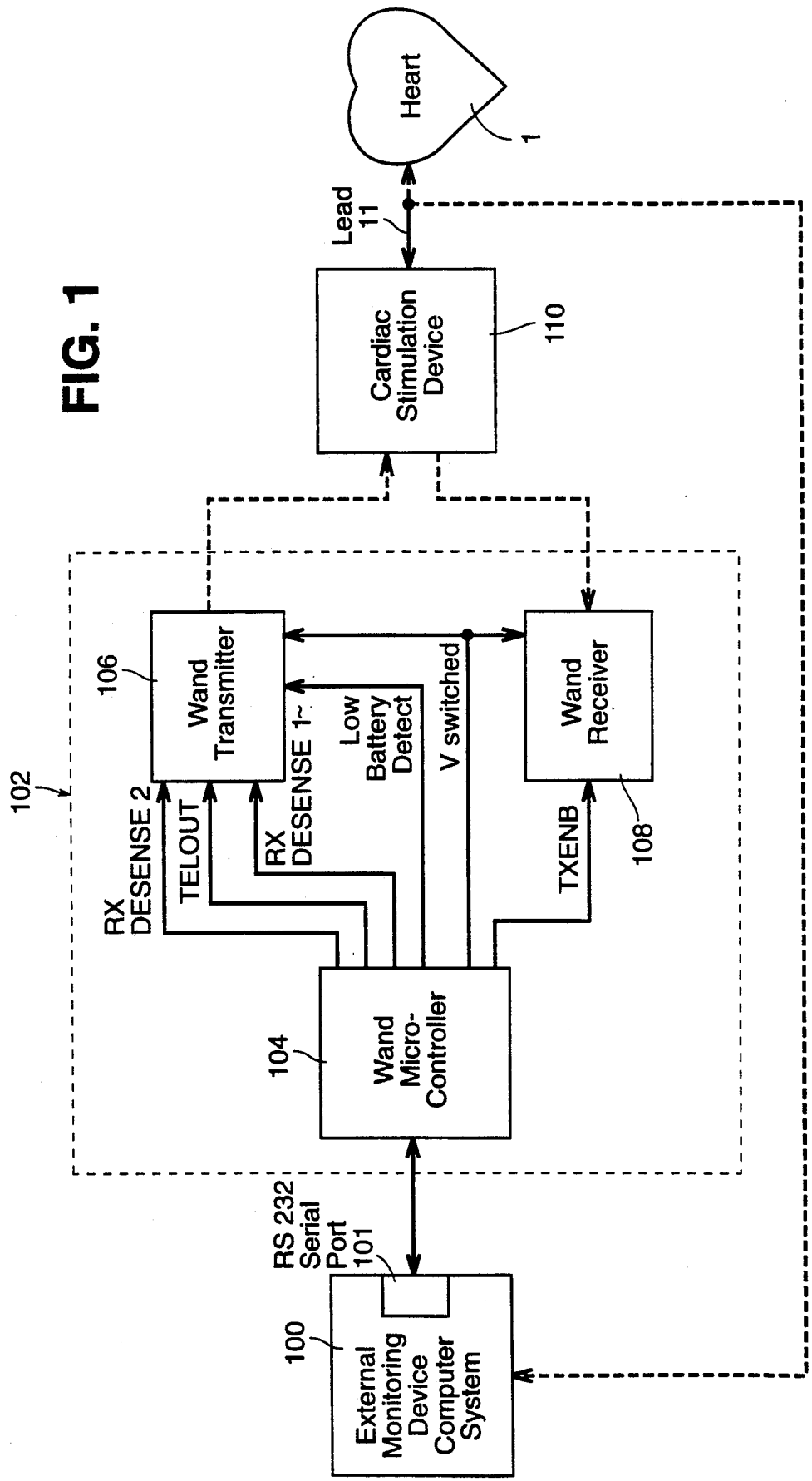
FIG. 1 is a high-level system block diagram showing the components of the present invention.

FIG. 1 is a high-level system block diagram showing the component blocks of the present invention, in which an external monitoring device computer system 100 communicates with an implantable cardiac stimulation device 110 by means of a programming wand 102, providing a telemetric communication link. The cardiac stimulation device 110 employs a lead 11, making an electrical connection to a heart 1 to stimulate the heart and to detect physiological signals from the heart. The programming wand 102 allows communication between the cardiac stimulation device 110 and the external monitoring device computer system 100 for monitoring and analysis of the physiological functionality of the heart 1.

The external monitoring device computer system 100 may be a standard personal computer (PC) system, which executes the programmer software as is known in the art of cardiac pacemakers, in addition to new functions provided by the present invention.

The programming wand 102 of FIG. 1 provides a communications interface between the external monitoring device computer system 100 and the implantable cardiac stimulation device 110. Bidirectional communication between the programming wand 102 and the computer system 100 takes place using a high speed RS-232 serial port 101. A wand microcontroller 104, within the programming wand 102, receives data and control signal information from the computer system 100 and drives a wand transmitter 106 to send this information to the cardiac stimulation device 110. This control information may be in the form of a request for the cardiac stimulation device 110 to transmit data such as operational parameters, intracardiac electrograms, physiological signals, information compiled from biological signals, and diagnostic test data back to the computer system 100 for analysis and display. As the cardiac stimulation device 110 complies with this request for information, the programming wand 102 receives, amplifies, filters and decodes telemetry signals sent by the cardiac stimulation device 110 and advances these signals to the external monitoring device computer system 100.

Physically, the programming wand 102 is a "mouse"-shaped housing (not shown) which contains circuitry for the wand microcontroller 104, the wand transmitter 106 and a wand receiver 108. The housing is connected by a coil cord (not shown) to a molded connector assembly (not shown) which connects to the RS-232 serial port 101 of the computer system 100. The connector assembly also contains a 9 volt battery (not shown), the power source for the programming wand 102.

The programming wand 102 includes functional circuits for the wand microcontroller 104, the wand transmitter 106 and the wand receiver 108.

Figure 2:
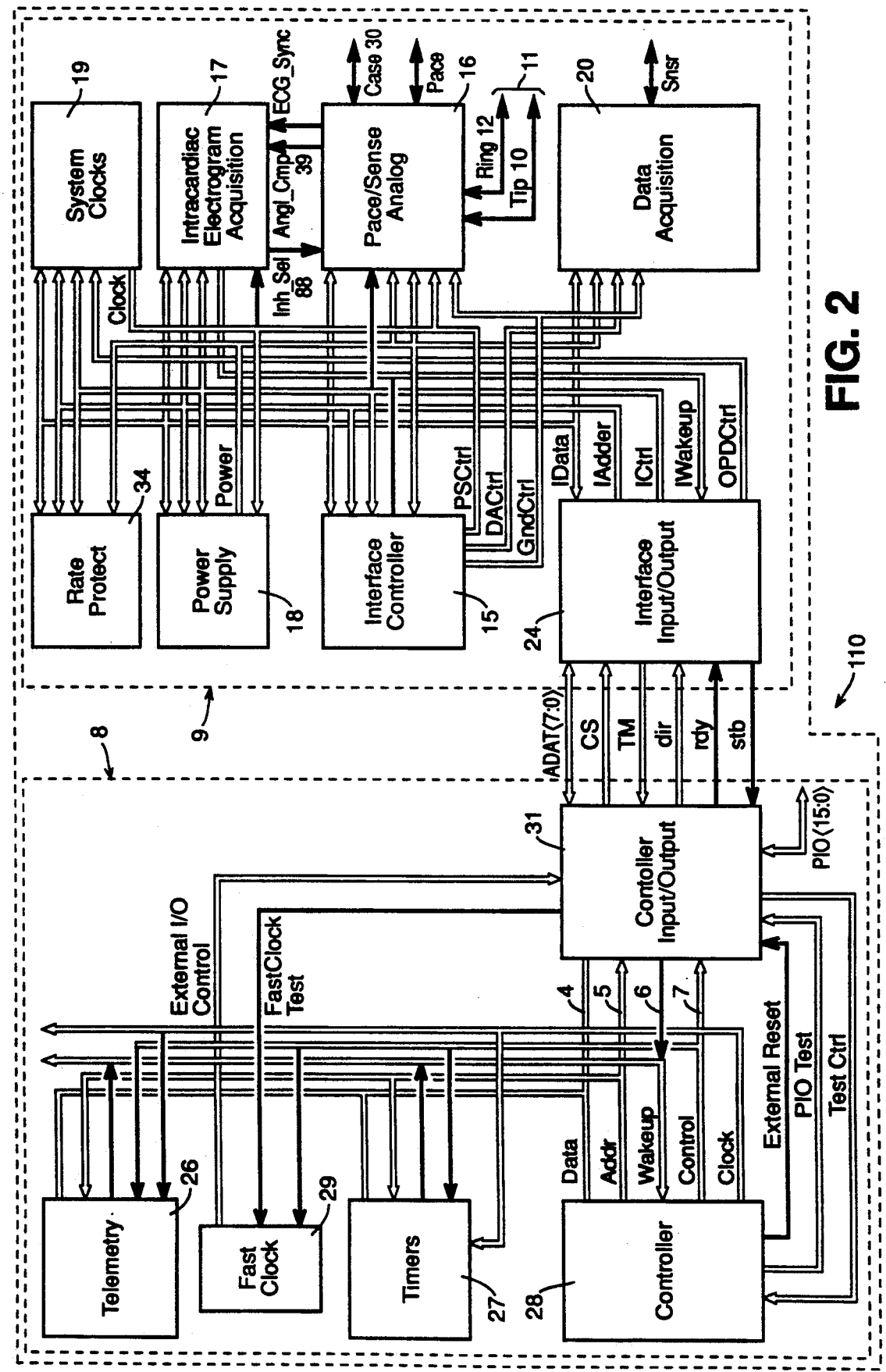
FIG. 2 is a high-level block schematic of an implantable cardiac stimulation device, a component of the present invention shown in FIG. 1.

The drawing of FIG. 2 is a high-level block schematic depicting the implantable cardiac stimulation device 110. A tip electrode 10 and a ring electrode 12, respectively, are those found in a conventional bipolar lead 11. The fundamental requirements for a cardiac stimulation device include the ability to generate and deliver, at selected intervals, electrical stimulation pulses of varying amplitudes and forms.

All implantable cardiac stimulation device 110 logic is under the control of a controller 28 (which may include a microprocessor), which controls all of the other blocks of FIG. 2. In the preferred embodiment of the invention, the controller 28 is a firmware-based microcontroller designed specifically for implantable applications. The controller 28 fetches micro-coded instructions from a control store ROM (not shown) located internal to the controller, executes these instructions and sequences to the next instruction. Control store ROM contains the executable control program instructions performed by the controller 28. The controller is inactive when no operations are pending, activates upon a "wakeup" command and executes other logic functions which are necessary in an algorithm-based implantable device. Logic blocks, such as a telemetry block 26, a timers 27 block, a pace/sense analog circuit 16, an interface controller 15 and an intracardiac electrogram acquisition circuit 17 generate wakeup commands which activate operations of the controller 28.

In particular, the controller 28 may, through command signals to the interface controller 15 and the pace/sense analog circuit 16, determine the amplitude and shape of stimulating pulses and also set the timing of pulse delivery. The controller 28 may also govern, in timing and number, the acquisition of intracardiac electrogram samples by reading registers within the intracardiac electrogram acquisition circuit 17. In addition, the controller 28 may, by setting switches within pace/sense analog circuit 16 and by performing computations internally, select and execute signal filtering procedures required for electrogram signal analysis. As the controller performs signal sampling, it carries out the analysis necessary for the diagnostic purposes of the device, as described below.

Input signals to the controller 28 are a system reset signal, a 32 kHz clock signal, four wakeup lines from external subsystems and various execution clock signals. Output signals which are provided by the controller 28 to other subsystems are a chipwide reset signal, various clock subharmonic signals, and digital data 4, address 5, and control 7 bus signals.

Telemetry block 26 is a conventional communications circuit in modern implanted cardiac stimulation devices, such as pacemakers, defibrillators and antitachycardia pacemakers. By means of an antenna (not shown), the telemetry block 26 allows for bidirectional communication of information between an external (not implanted) programming device or programmer, such as the external monitoring device computer system 100 (FIG. 1), and the implantable cardiac stimulation device 110. Communication permits both an adjustment of the data acquisition parameters from the external programmer and transmission of information from the implanted device to the external device. The information transmitted from the implanted cardiac stimulation device 110 to the external programmer 100 may include accumulated data and a signal representative of the instantaneous sensed intracardiac electrogram. Present-day sophisticated telemetry circuits allow for the interrogation of stored diagnostic data and the derivation of real-time operational data. These operations are discussed in more detail hereinafter in connection with the description of FIG. S.

Referring again to FIG. 2, the implantable cardiac stimulation device 110 uses timers 27 to measure various time intervals and provide timing control for circuit operations, physiological stimulation or real time events. The timers 27 block includes circuits to provide three independent interval timers timer 0, timer 1 and timer 2 (not shown). The controller 28 writes timing initialization and duration information to timers 27. The timers 27 respond by generating and transmitting corresponding wake-up signals T0, T1 and T2, via wakeup lines 6, to the controller 28, after respective time intervals for timer 0, timer 1 or timer 2 expire. The controller 28 determines the duration of these time intervals by writing initialization and duration codes to control registers (not shown) within the timers 27. Timer 0 may be individually initialized to specify a timing resolution of 30 μs, 1 ms, 4 ms or 8 ms. The two remaining interval timers, timer 1 and timer 2, each may be individually initialized to specify a timing resolution of 1 ms, 4 ms or 8 ms. The controller employs timer wake-ups to govern the timing of cardiac cycles as well as to time short-term intervals for miscellaneous operations. One operation employing the timers 27 is the setting of timing for sampling intervals in intracardiac electrogram acquisition. Furthermore, the controller uses timer wake-up signals to control a real-time clock function that determines the length of time since manufacture of the device and initiates long-term housekeeping functions.

Each of the three interval timers within timers 27 includes a pair of memory-mapped 8-bit registers (not shown), a prescaler register (not shown) and a timer register (not shown). When the controller 28 writes a data byte to the prescaler register, the value of the least significant two bits of the data byte determines the resolution of the associated interval timer. The controller 28 may then write a data byte to the appropriate timer register (for timer 0, timer 1 or timer 2) to determine the number of counts at the prescaler resolution before a wakeup occurs.

A controller input/output block 31 supports external input and output functions so that a processor subsystem 8, which includes the controller 28, the timers 27, the telemetry block 26 and a fast clock 29, can read and write data to and from external data lines to various source and destination subsystems, such as an interface subsystem 9 of FIG. 2. The controller input/output block 31 is an interface to external devices (not shown) that supports read and write operations to control/status and data registers in such external devices. Controller input/output block 31 provides for three modes of communication: memory-mapped input and output, a parallel input and output, and test modes.

An interface input/output block 24 provides an interface between the controller input/output block 31 of the processor subsystem 8 and an interface subsystem 9 which includes interface controller 15, pace/sense analog circuit 16, a data acquisition circuit 20, intracardiac electrogram acquisition circuit 17, a rate protection circuit 34, system clocks 19 (which supply stable crystal-controlled clock signals for numerous timing functions within the processor 8 and the interface 9 subsystems) and a power supply 18 (which furnishes the energy needs of the processor 8 and interface 9 subsystems). The interface input/output block 24 communicates with the controller input/output block 31 over an 8-bit bus ADAT<7:0> which is multiplexed to communicate address and data information, and three control signals rdy, stb and dir to demultiplex and latch the address signals and provide direction control for data transmission. The controller input/output block 31 provides data and address lines ADAT<7:0> to the interface input/output block 24 and governs the operation of interface control signal lines, including data direction dir, ready rdy and strobe stb signal lines. The interface between the controller input/output block 31 and the interface input/output block 24 also includes chip select lines CS, allowing interfacing of multiple interface subsystem 9 with a single processor subsystem 8, and test mode lines TM, providing for testing of the interface subsystem 9.

The interface input/output block 24 provides wakeup control signals on the bus ADAT<7:0> to the controller input/output block 31 to activate wakeup processing within the controller 28. The interface input/output block 24 controls wakeup lines, which are internal to the interface subsystem 9 and are separate from the wakeup lines within the processor subsystem 8.

The interface input/output block 24 includes memory-mapped registers (not shown) for processing wakeups. These registers are accessed by the controller 28 via the data bus ADAT<7:0>. The interface input/output block 24 generates wakeup signals arising from various circuits within the interface subsystem 9. These registers allow the controller 28 to control wakeups generated by the interface subsystem 9 in a manner similar to that which the controller 28 uses to control processor subsystem 8 wakeups. The controller 28 regulates the operation of the interface wakeups using read and write operations to the interface wakeup registers over the bus ADAT<7:0>. The controller 28 may read an interface wakeup flag set register (not shown) to determine whether a particular interface wakeup has occurred and write to this register to force a wakeup to occur without regard to the state of the operations which normally activate such a wakeup. The controller 28 may write to the interface wakeup flag reset register (not shown) to clear an interface wakeup flag (not shown). The controller 28 may write to the interface wakeup mask register to prevent interface operations which might activate a wakeup. An interface priority encoder circuit (not shown) within the interface input-/output block 24, responds to an interface wakeup signal IWakeup by identifying the signal causing the interface wakeup and encoding this identity for reading by the controller 28 over the bus ADAT<7:0>.

An interface controller 15, upon receiving commands from the controller 28 via the interface input/output block 24, generates timed sequences of latched control signals to control the operations of the data acquisition circuit 20, the pace/sense analog circuit 16 and the power supply 18. The interface controller 15 starts each sequence, as designated and initiated by the controller 28, and provides a wakeup signal to the controller 28 when the sequence is finished.

The interface controller 15 communicates to other circuits within the interface subsystem 9 via subsystem-wide data, address and control buses IData, IAddr and ICtrl, respectively. Timing signals are provided for the interface subsystem 9 on 16 kHz and 131 kHz clock lines (not shown). The interface controller 15 also sets latched control signals for various of the interface subsystem circuits. The state of all control signals at one time, in combination with control information for the interface controller 15 itself, is called an image.

Under the direction of the controller 28, via signals on line DACtrl from the interface controller 15, the data acquisition circuit 20 performs sensor measurements, using line Snsr. In addition, the data acquisition circuit 20 sets the output voltage prior to any generation of a stimulation pulse.

Figure 3:
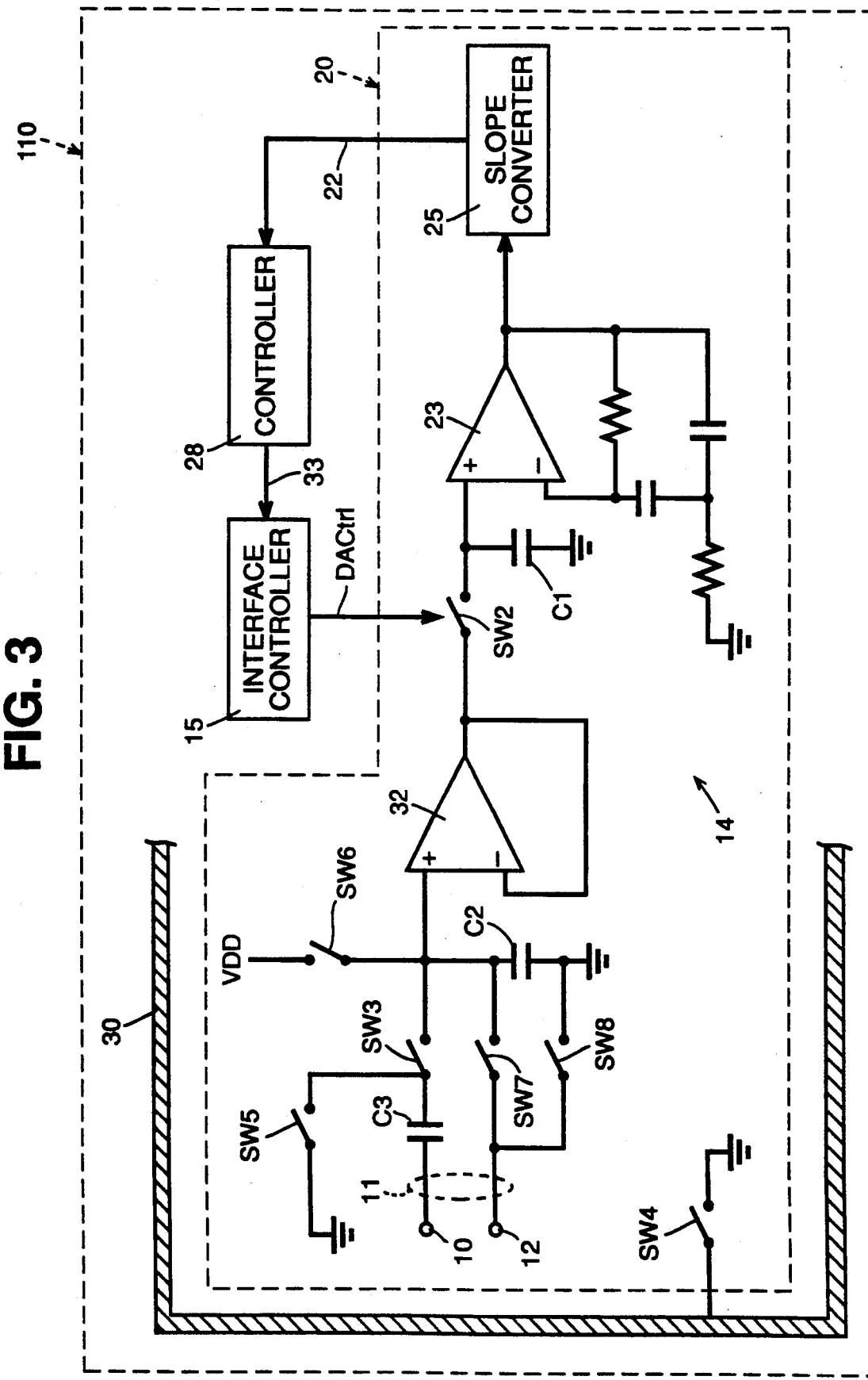
FIG. 3 depicts an embodiment of an impedance measurement circuit, forming part of the cardiac stimulation device shown in FIG. 1, which operates in a pulsed mode.

The controller 28 directly writes calibration codes to memory-mapped registers within the data acquisition circuit 20 to adjust measurements to reference measurement signal levels. In general, the controller 28 activates a measurement, or other operation, by writing a measurement-identifying command to the interface controller 15. In turn, the interface controller 15 carries out the measurement by generating signals which act on the data acquisition circuit 20. There are two types of measurements—sensor and diagnostic self-test measurements. The data acquisition circuit 20 performs all measurements of both types by differential sampling. In the first step of the differential sampling procedure, the data acquisition circuit 20 sets switches to sample a particular predetermined reference signal 3 and then stores the reference sample value on a first capacitor (not shown). All measurements are performed by measuring the voltage which is generated across a sensor resistance (not shown) by an injected constant-current source. Next, the data acquisition circuit 20 sets switches to sample a predetermined test signal, subtracts the reference sample value from the test sample value, and stores the test sample value on a second capacitor (not shown). The data acquisition circuit 20 may attenuate either or both the reference signal and the test signal prior to sampling. The data acquisition circuit 20 then places the sample value in a digital form by performing slope conversion on the signal stored on the second capacitor. A slope converter 25, shown in FIG. 3, is a counter within the data acquisition circuit 20 of FIG. 2, which times the interval required to charge a third capacitor (not shown) from 0 V to the voltage on the second capacitor (the differential test voltage) using a known current source. Following the completion of a measurement, the controller 28 may read the result of the measurement operation from a memory mapped 10-bit measurement result register within the data acquisition circuit 20 of FIG. 2. The measurement result register is communicated from the data acquisition circuit 20 to the controller 28 via the IData bus in the interface subsystem 9 and the Data bus 4 in the processor subsystem 8, but this data path is shown in FIG. 3 by the measurement result line 22 to simplify the discussion herein.

Referring back to FIG. 2, the data acquisition circuit 20 may perform one or more sensor measurements with respect to a group of sensors (not shown), including a temperature sensor, a pressure sensor, an ultrasound sensor and an impedance sensor which may be configured to measure respiration, cardiac contraction or body motion. The impedance sensor measurements and the temperature sensor measurement both employ a detection of resistance change from a DC value. Two examples of respiration sensing are more fully described in U.S. Pat. No. 4,702,253, entitled "Metabolic-Demand Pacemaker and Method of Using the Same to Determine Minute Volume", issued to T. A. Nappholz et al. on Oct. 27, 1987, and in U.S. Pat. No. 4,901,725, entitled "Minute Volume Rate-Responsive Pacemaker", issued to T. A. Nappholz et al. on Feb. 20, 1990. A temperature sensor is described in U.S. Pat. No. 4,688,573, entitled "Temperature Driven Rate Responsive cardiac Pacemaker", issued to Alt on Aug. 25, 1987. A pressure sensor is disclosed in U.S. Pat. No. 4,566,456, entitled "Apparatus and Method for Adjusting Heart/Pacer Rate Relative to Right Ventricular Systolic Pressure to Obtain a Required Cardiac Output", issued to Koning et al. on Jan. 28, 1986. An ultrasound sensor is described in U.S. Pat. No. 5,188,106, entitled "Method and Apparatus for Chronically Monitoring the Hemodynamic State of a Patient Using Doppler Ultrasound", issued to Nappholz et al. on Feb. 23, 1993.

The cardiac stimulation device 110 makes an impedance measurement when the controller 28 activates an impedance measurement circuit, hereinafter described in connection with a discussion of FIG. 3, that is within the data acquisition circuit 20. The data acquisition circuit 20 may perform the impedance measurement in either of two modes, as selected according to commands received from the controller 28. In a first measurement mode, a bipolar mode, the data acquisition circuit 20 injects a current into the body through the ring electrode 12, with the return current flow connection at the case 30. While the data acquisition circuit 20 applies the current pulse to the body, it measures the voltage between the tip electrode 10 and the case 30. Next, to balance the charges applied to the body, the data acquisition circuit 20 applies a current pulse which flows from the case 30 to the ring electrode 12. The total current applied in the balancing pulse matches the total current of the measurement pulse. For example, a 1.0 mA measurement pulse which is applied for 8 $\mu$s is balanced by a balancing pulse of 0.125 mA with a duration of 64 μs.

In a second measurement mode, a unipolar mode, the data acquisition circuit 20 injects a current into the body through the tip electrode 10, with the return current flow connection at the case 30. The measuring current which is applied to the electrode has frequency characteristics in the range from about 10 kHz to about 1000 MHz. At these measuring current frequencies, the lead 11 acts as an antenna which creates a displacement current in the body. The impedance measuring circuit 14 may generate this measuring current in the form of a continuous wave current, short-duration pulses of current, or timed pulses of continuous wave current. The impedance measurement circuit 14 measures spatial impedance by determining the potential between the case 30 and the cardiac stimulation device 110 input connection to the conductor (not shown) within the lead 11. This conductor extends to the tip electrode 10. In this configuration, the case 30 serves as a reference potential for the cardiac stimulation device circuitry. When the impedance measurement circuit 14 generates measuring currents at appropriate frequencies, as will be described hereinafter, the impedance measurement reflects respiration to a much greater extent than it indicates cardiac contraction or body motion.

The preferred embodiment of the implantable cardiac stimulation device 110 samples the respiration signal at a 20 Hz rate and performs bandpass filtering on the sampled signal. An exemplary two-pole bandpass filter 30 may have cutoff frequencies, wherein the gain is reduced by a factor of two (6 dB), at 0.05 Hz (highpass) and 0.80 Hz (lowpass).

FIG. 3 illustrates an embodiment of the impedance measurement circuit 14 which can operate in either of the aforementioned first bipolar and second unipolar measurement modes using a pulsed measurement current. The impedance measurement circuit 14 includes a connection through a switch SW4 with the case 30, a connection through switches SW7 and SW8 with the ring electrode 12 and a connection through a switch SW3 with the tip electrode 10 (via the lead 11). The tip electrode 10 is a conventional pacing/sensing electrode. The indifferent electrode is the case 30. In the first bipolar mode, the impedance measuring circuit 14 applies a source measuring current to the patient's body using the ring electrode 12 and measures the voltage between the case 30 and the tip electrode 10 to determine the impedance. In the second unipolar mode, the impedance measurement circuit 14 employs the tip electrode 10 and lead 11 both for applying a source measuring current to the patient's body, and for measuring the impedance between the tip electrode 10, lead 11 and the case 30. A buffer 32 and filter 23 are also employed in circuit 14.

All switches in FIG. 3 are indirectly under the control of controller 28 via processing by the interface controller 15 using memory-mapped register communication. The controller 28 sends command identification codes to a memory-mapped register, data acquisition/pace sense (DAPS, not shown) within the interface controller 15, via a line 33. The interface controller 15, in response to these command codes, sets and resets control signals within the data acquisition controller 20 (FIG. 2) to perform various measurements. One control signal from the interface controller 15 is shown extending via a bus DACtrl (data acquisition control) to switch SW2, but it is to be understood that the switches SW3, SW4, SW5 and SW6 are similarly controlled. The interface controller 15 closes switch SW6 to charge a measuring capacitor C2 to a regulated voltage source VDD. Subsequently, the interface controller 15 opens switch SW6 and closes switches SW3 and SW4 for a predetermined measuring interval ΔT, while switch SW5 is held open, thereby connecting measuring capacitor C2 to lead 11 through a coupling capacitor C3. While the switches SW3 and SW4 are closed, measuring capacitor C2 discharges through capacitor C3 into the lead 11, thereby decreasing the voltage across measuring capacitor C2. The amount by which the voltage across measuring capacitor C2 diminishes depends on the impedance of the lead-tip combination and the impedance of the surrounding tissue. The impedance of the lead-tip combination is known and the impedance of the surrounding tissue is the object of the measurement. Measuring capacitor C2 stores the voltage which buffer 32 later transfers to the measuring circuit. After the predetermined measuring time interval ΔT, the interface controller 15 opens switches SW3 and SW4, allowing the buffer 32 to access the voltage held on the measuring capacitor C2. This voltage is advanced through the buffer amplifier 32 and switch SW2 (which the interface controller 15 closes at the time it opens switches SW3 and SW4), and is sampled on capacitor C1 at the input of the filter 23. Then for the next measuring cycle, the interface controller 15 opens switch SW2 and closes switch SW6 to charge measuring capacitor C2 for the next measurement. In the preferred embodiment of the invention, the controller 28 requests the measurement of impedance twenty times per second. For each measurement, the interface controller 15 closes the switches SW3 and SW4 for a pulse duration of 250 ns, during which the voltage across the capacitor C2 is placed on the lead 11. The resistors and capacitors associated with filter 23 pass frequencies between about 0.05 Hz and 0.8 Hz, the standard range for respiratory measurements.

The value of the measuring capacitor C2 is selected to store the range of voltages which result from various body impedances. In one embodiment of the invention, C2 has a capacitance of 4.7 nF. The coupling capacitor C3 provides for DC isolation for the input to the measuring circuit. In one embodiment of the invention, the coupling capacitor C3 has a value of about 7.5 μF, which effectively eliminates the influence of the DC voltage on measurements.

The analog signal output of the filter 23 passes to the slope converter 25 within the data acquisition block 20, which provides a digital signal output to the aforementioned memory-wrapped 10-bit measurement result register (not shown), which is also within the data acquisition block 20. The digital signal output of the measurement result register is read via line 22 by the controller 28 for processing, as is hereinafter described in connection with a discussion of FIG. 5.

Figure 4:
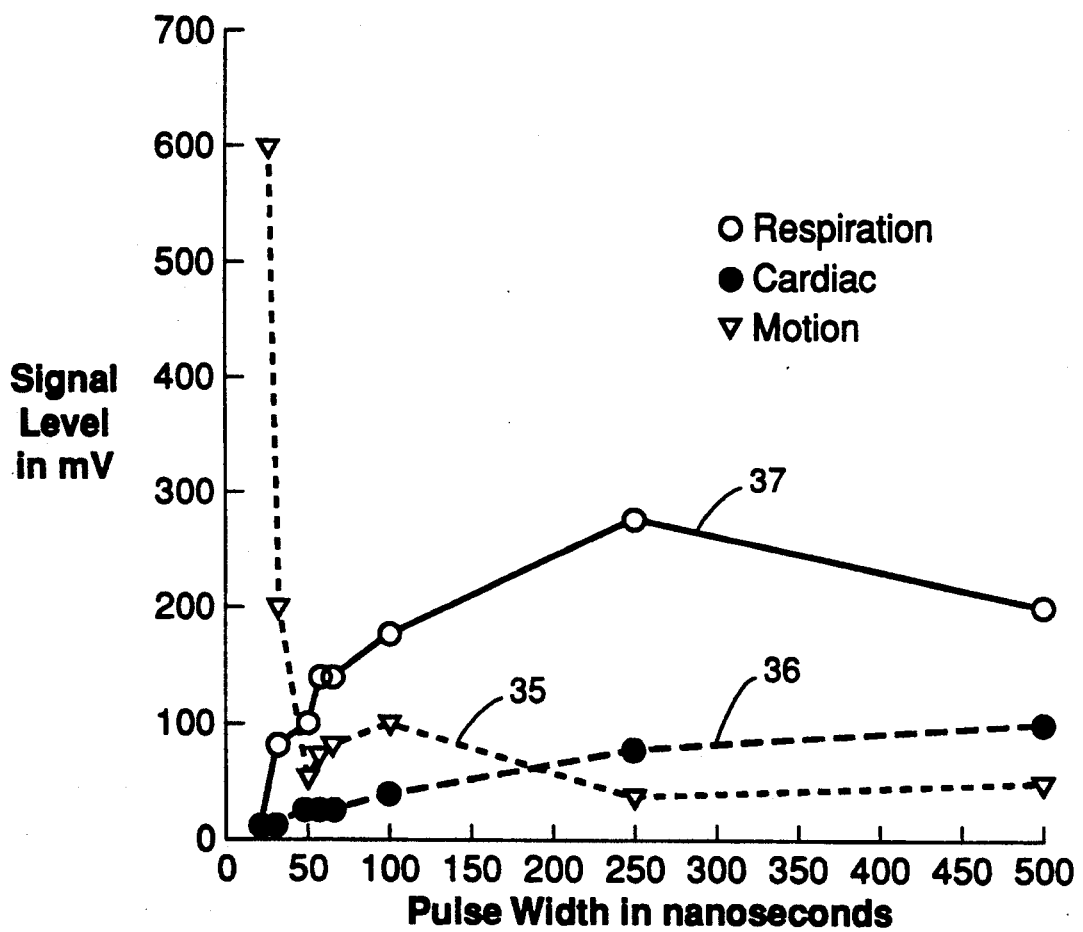
FIG. 4 is a graph which characterizes the relative signal levels of different physiological and nonphysiological signals detected by the circuit of FIG. 3 when it interrogates a patient's body with current pulses of various pulse widths.

During a measurement interval, signals from the interface controller 15 briefly disable pace and sense functions. Although sensing is disabled while the impedance measurement is taking place, the duration of the measurement is on the order of fractions of microseconds a time so short relative to that of heart signals that the disabling of sensing during this time is of no importance. A The graph of FIG. 4 characterizes the relative levels of different physiological and non-physiological signals which are detected by the circuit of FIG. 3 when it interrogates a patient's body with current pulses of different widths. The cardiac stimulation device 110 can "tune" the impedance sensor to measure a particular type of signal and reject unwanted signals and other noise by selecting a particular measuring current pulse width. At very short pulse widths (e.g., 60 to 200 nanoseconds) motion artifact signals have the largest amplitude, as shown by "motion" curve 35. The amplitude of physiological signals arising from the heart steadily rises with increasing pulse width duration, as shown by "cardiac" curve 36. The amplitude of respiratory signals abruptly rises with increasing pulse duration to pulse widths of about 250 ns, then decreases for larger pulse width durations, as shown by "respiration" curve 37. The minute volume controlled metabolic demand cardiac stimulation device of the present invention seeks a preferred pulse width of about 250 ns, which provides the best respiratory signal to noise ratio. A pulse width of this duration (250 ns) lessens the influence of cardiac signal "noise", avoids interface electrolytic phenomena, but still reduces the influence of motion artifacts.

By selecting different values of measuring current frequency or pulse width, a pulse generator can "tune" an impedance sensor to measure a particular type of signal and reject unwanted signals and other noise. The impedance measurement circuit 14 measures the impedance between the input connection of the lead 11 to the stimulation device 110, and the case 30 of the device. The circuit thus senses body impedance along the entire length of the lead. The impedance at the lead input connection is the impedance due to multiple reflections of the signal along the lead due to the properties of the lead and the medium surrounding it. At high measuring frequencies, a larger portion of the signal leaks from the lead close to the case. At lower measuring frequencies, more of the signal will leak from the lead further along the lead. Some of the sensed signals may be physiological, others may arise from intrinsic sources. For example, at a particular range of measuring current frequencies, respiration signals predominate. At another range of frequencies, cardiac stroke volume signals will dominate. At still another range of frequencies, noise caused by motion may be the primary signal.

The impedance measurement circuit 14 of FIG. 3 derives digital spatial impedance samples, in the form of 10-bit data bytes having values ranging from −512 to +513, at a rate of about 20 per second and communicates these samples to the controller 28 by means of the aforesaid measurement result register of data acquisition block 20 and line 22. Negative digital signals carried by the measurement result line 22 indicate that the analog respiration signal is decreasing, while positive digital signals signify an increasing signal. The data in the measurement result line 22 may be read and formatted by the controller 28 and transmitted to an external monitoring computer system 100 (FIG. 1) to provide for analysis of a respiration signal.

Figure 5:
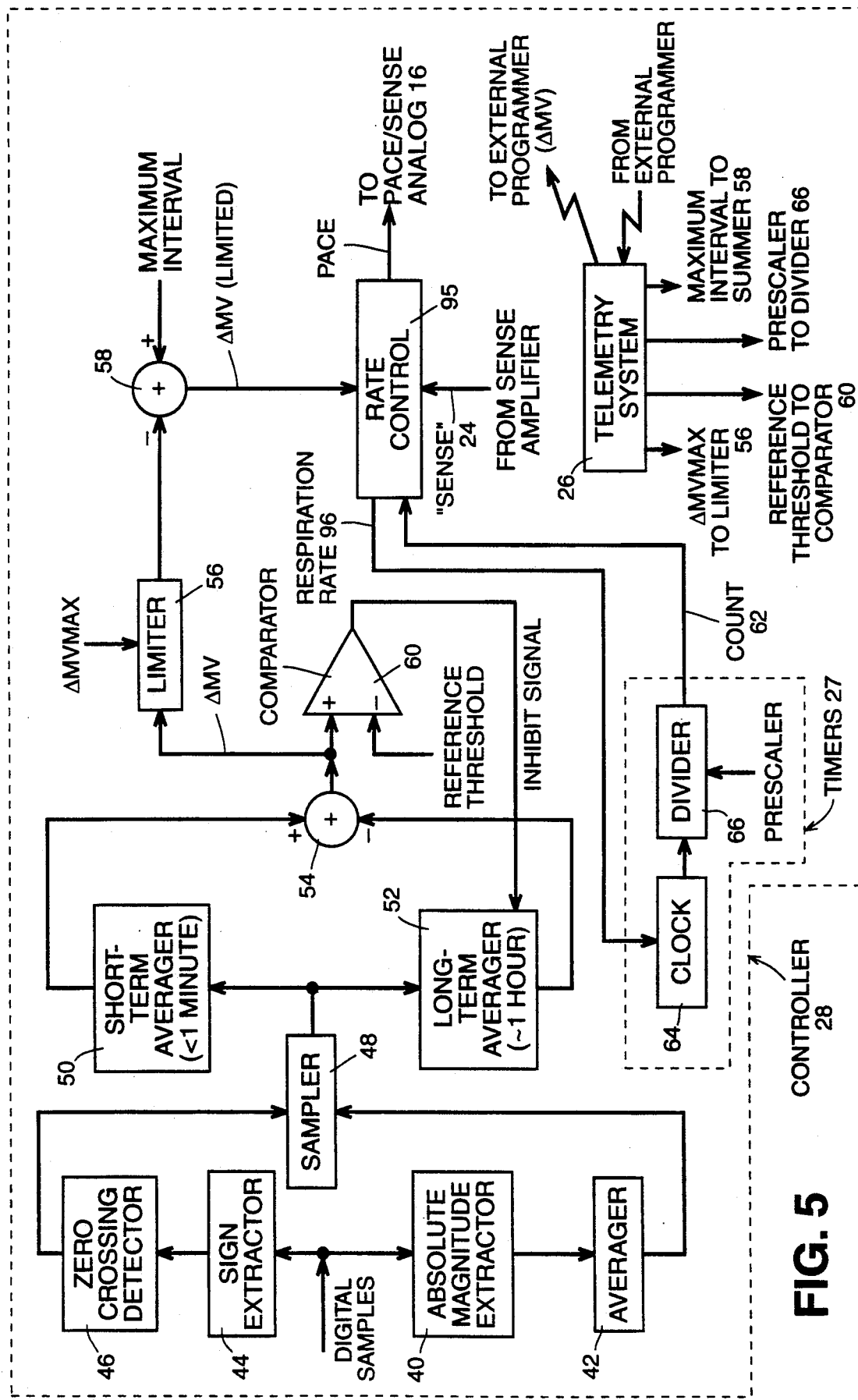
FIG. 5 depicts a block diagram identifying the functional operations performed by a controller, shown in block form in FIG. 2, which operate on digital samples of the impedance measurement to derive pace commands that are sent to a pulse generator, also shown in block form in FIG. 2.

Referring to FIG. 5, in which the firmware program blocks of controller 28 are shown in greater detail, the manner of deriving a minute volume measurement from the digital samples provided by the impedance measurement circuit 14 of FIG. 3 is illustrated. A firmware bandpass filter and absolute magnitude extractor 40 bandpass filters the impedance signal to yield a passband from about 0.5 Hz to approximately 0.8 Hz and derives the absolute magnitude of each digital sample (i.e., negatively signed samples are changed to positive samples of the same amplitude). In the preferred embodiment of the invention, the bandpass filter 40 is implemented in the form of three cascaded filter operations, as is described by the equations 1, 2 and 3, below. A first lowpass filter operation is described by equation 1:

$$A_1(n) = ((\tfrac{1}{1})*A_1(n-1)) + 256*X(n), \qquad (1)$$

in which $A_1(n)$ is the output of the first lowpass filter operation for the current timed data sample, $A_1(n-1)$ is the output of the first lowpass filter operation for the previous timed data sample and $X(n)$ is the current timed data within the measurement result register that feeds line 22 of FIG. 3. The result of the first lowpass filter operation $A_1(n)$ is then applied to a second lowpass filter operation, which is described by equation 2:

$$A_2(n) = ((255/256)*A_2(n)) + (1/256)*A_1(n), \qquad (2)$$

in which $A_2(n)$ is the output of the second lowpass filter operation for the current timed data sample. The result of the second lowpass filter operation $A_2(n)$ is applied to a first difference highpass filter operation, which is described by equation 3:

$$Y(n) = (A_2(n) - A_2(n-1))/256, \qquad (3)$$

where $Y(n)$ is the current output of the bandpass filter 40. The absolute magnitude of the signal is obtained by averaging the output signal $Y(n)$, as is shown in Equation 4:

$$Y_{avg} = \sum_{n=1}^{16} abs(Y(n)), \qquad (4)$$

in which $Y_{avg}$ is the current absolute magnitude of the impedance signal.

In the preferred embodiment of the invention, equation 5, below, is a filter operation which operates at 20 Hz. Samples of the rectified impedance signal are added for sixteen cycles, the total at the end of the sixteenth cycle is output, and then the sum is set to zero. Over long periods of time, the average value of the digital samples is zero because the filter 23 (FIG. 3) in the impedance measurement circuit 14 has a gain of one for a DC input. By eliminating the sign from all samples in the absolute magnitude operation of block 40, an averager 42 derives a running average of the absolute magnitudes of the samples. The time constant of the averager is short (e.g., about 25 seconds) so that the digital value at its output represents the average respiratory tidal volume over a few breaths. The absolute magnitude value of each sample represents the respiratory impedance signal. Therefore, the controller 28 adds and averages a sequence of these absolute magnitude sample values in averager block 42 to provide a measure of the respiratory tidal volume in the manner of equation 5:

$$A_3(n) = (15/16)*A_3(n-1) + H_{avg}, \qquad (5)$$

where $A_3(n)$ is the current tidal volume signal.

A sign extractor 44 monitors only the signs, and not the magnitudes, of the digital samples on the memory-mapped measurement result register which feeds line 22 of FIG. 3 to provide for zero crossing detection. The sign extractor 44 delivers successive bits, each of which represents the sign of a digital sample, to a zero crossing detector 46. The zero crossing detector 46 monitors respiration rate by ascertaining the timing of changes in the polarity of the impedance measurement signal. Generally, a zero crossing occurs whenever the sign of a digital sample differs from the sign of the immediately preceding digital sample. However, there are physiological limits to respiration rate and, therefore, to the frequency of zero crossings. Zero crossings occurring at a rate higher than a predetermined physiological limit must indicate the presence of a noisy respiration signal. Thus, the zero crossing detector analyzes the signs of a quantity (for example 10) of the most recently acquired samples and determines whether a defined preponderance of samples (for example 7 of 10) have a particular sign. If so, and if the last zero crossing operation which found a preponderance of a particular sign determined that the majority had an opposite sign, the zero crossing detector 46 presumes the occurrence of a zero crossing. When the sign changes, the zero crossing detector 46 triggers a sampler 48 to read the average value represented by the current value presented by the averager 42. The data from the sampler 48 may be read and formatted by the controller 28 (FIG. 2) and transmitted to the external monitoring computer system 100 (FIG. 1) to provide for analysis of the tidal volume signal. The sampler 48 delivers this average value to both a short-term averager 50 and a long-term averager 52. In the preferred embodiment of the invention, the equation for the short-term averager 50 is given by equation 6:

$$A_4(n) = ((2^{M_4}-1)/2^{M_4}) * A_4(n-1) + A_3(n), \quad (6)$$

where $A_4(n)$ is the current output of the short-term averager 50, $A_4(n-1)$ is the previous output of the short-term averager and $M_4$ is a coefficient which determines the programmable cutoff frequency of the short-term averager. $M_4$ is a number from 3 to 5, which results in cutoff frequencies of $3.1*10^{-3}$ Hz, $6.2*10^{-3}$ Hz and $12.4*10^{-3}$ Hz. The equation for the long-term averager 52 is given by equation 7:

$$A_5(n) = ((2^{M_5}-1)/2^{M_5}) * A_5(n-1) + A_4(n), \quad (7)$$

where $A_5(n)$ is the current output of the long-term averager 52, $A_5(n-1)$ is the previous output of the long-term averager and $M_5$ is a coefficient which determines the programmable cutoff frequency of the long-term averager. $M_5$ is programmed to either 10 or 16, which results in cutoff frequencies of $97*10^{-6}$ Hz or $1.52*10^{-6}$ Hz.

The zero crossing detector 46 pulses its output twice, and the sampler 48 samples twice, during each breath, when the impedance signal crosses zero during exhalation and during inhalation. The zero crossing detector 46 employs the previously described preponderance of samples, or "majority vote", technique to sense a zero crossing, in which the detector assumes an occurrence of a zero crossing when a predetermined proportion of the most recent samples have a sign opposite to that of the sign determined after the last zero crossing. In the preferred embodiment of the invention, at least 70% of the most recent samples in the last 0.5 second must have a sign opposite to that of the sign determined after the last zero crossing.

Each average value sample at the output of averager 42 represents the tidal volume, the average of the last few integrals of the respiratory impedance signal. The short-term averager 50 and the long-term averager 52 derive values which are dependent not only on the magnitudes of the samples, but also upon the rate of the oscillating respiratory signal, as determined by the zero crossing detector 46. Because the long-term and short-term averagers update and accumulate samples at each zero crossing event, the long-term and short-term minute volume values reflect the rate of breathing as well as the depth of breathing.

As shown in FIG. 5, a slimmer 54 derives $\Delta MV$, the difference between the short-term averaged and long-term averaged minute volume signals. $\Delta MV$ is the control signal which drives the pacing rate. As the short-term average increases relative to the long-term average, representing an increasing metabolic demand, the pacing rate increases. Conversely, when $\Delta MV$ decreases, the pacing rate decreases.

The $\Delta MV$ value at any instant is the input to a limiter 56, which compares $\Delta MV$ to $\Delta MVMAX$, a predetermined value which serves as the maximum $\Delta MV$ value allowed to control the pacing rate. The limiter 56 applies the current value of $\Delta MV$, or $\Delta MVMAX$ if it is smaller than $\Delta MV$, to the minus input of a summer 58. The summer 58 compares the output of limiter 56 to maximum interval, a quantity applied at the plus input of summer 58 which represents an offset corresponding to a physician-determined minimum pacing rate. Summer 58 continuously presents its output $\Delta MV$ (limited), a difference value, to the input of a rate control block 95, which compares the $\Delta MV$ value to a tabular array in controller 28 data RAM. The values in the tabular array, which are previously determined by programming, correspond to pacing cycle intervals and, therefore, are used to determine a respiration-determined pacing rate, called respiration rate 96.

Within a timers block 27, there is a clock 64, which applies pulses to a divider 66 and divides the clock pulses by a quantity referred to as a prescaler to generate a count 62, corresponding to time intervals of a predetermined duration. The rate control block 95 writes the respiration rate 96 to the clock 64 at the end of a pacing cycle, which occurs upon the first event of either receipt of a "SENSE" signal 24 from the sense amplifier (within pace/sense analog block 16 of FIG. 2) or a time out of count 62 (to a value of zero). Both the clock 64 and the divider 66 are components of timers block 27, but are discussed here separately to clarify their function with regard to FIG. 5. Count 62 decrements whenever a pulse appears at the output of divider 66. When the count 62 decrements to zero, it produces a pulse through signals from the controller 28 to the interface controller 15, which activates a pacing pulse via pace/sense analog circuit 16. If the pace/sense analog circuit 16 of FIG. 2 senses a natural heartbeat before the count 62 decrements to zero, a timeout wakeup occurs, causing the controller 28 to evoke a pacing stimulation pulse. In either case, the controller 28 loads the difference value from summer 58 to initialize the escape interval of the cardiac stimulation device. The escape interval is the time between a paced or sensed cardiac event and the subsequent pacing stimulus. In this manner, the cardiac stimulation device may operate in a standard inhibited mode except that the minute volume measurement determines the pacing rate. As the quantity $\Delta MV$ increases, the simmer 58 derives a smaller difference value ("maximum interval" minus $\Delta MV$) that it presents to the rate control block 95. This, in turn, means that the pacing rate increases, as is required for a larger $\Delta MV$. When $\Delta MV$ is zero, the summer 58 presents the maximum interval value to the rate control block 95, which results in the minimum pacing rate, precisely what is required when there is no metabolic demand beyond that provided by the minimum pacing rate. The quantity "maximum interval" is simply the interval which corresponds to the minimum rate.

Conventional pacemakers include telemetry systems, as represented by telemetry block 26 of FIG. 2, which allow a physician to program parameters such as minimum rate, as well as the prescaler value, ΔMVMAX, and a reference threshold which is applied to comparator 60 and will be described below. The method of derivation of these programmable parameters is disclosed in the description of the pacemaker in the aforesaid U.S. Pat. No. 4,901,725.

Again referring to FIG. 5, the output of slimmer 54 is input, not only to the limiter 56, but also to the plus input of a comparator 60. The telemetrically-programmed reference threshold feeds the minus input of the comparator. Whenever ΔMV exceeds the reference threshold, the output of the comparator goes high and inhibits the long-term averager 52. In effect, a large value of ΔMV represents a metabolic demand which is associated with an exercising patient. Until the patient stops exercising, the long-term average does not increase. If it were allowed to increase, after an hour or more the long-term average would approach the value of the short-term average, ΔMV would diminish and the pacing rate would drop from its original high value. Once the patient begins exercising and the pacing rate increases, it is not desirable that the rate decrease simply due to the elapse of time. For this reason, the cardiac stimulation device fixes the long-term average. When the patient stops exercising and the short-term average decreases, ΔMV will fall below the reference threshold and the long-term average will again track the short-term average in the usual manner. In the illustrative embodiment of the invention, the reference threshold is equal to one-half of the ΔMVMAX, unless the physician programs the value differently. This technique allows long-term adaptation to a basal minute volume measurement level while still allowing extended periods of exercise.

Figure 6:
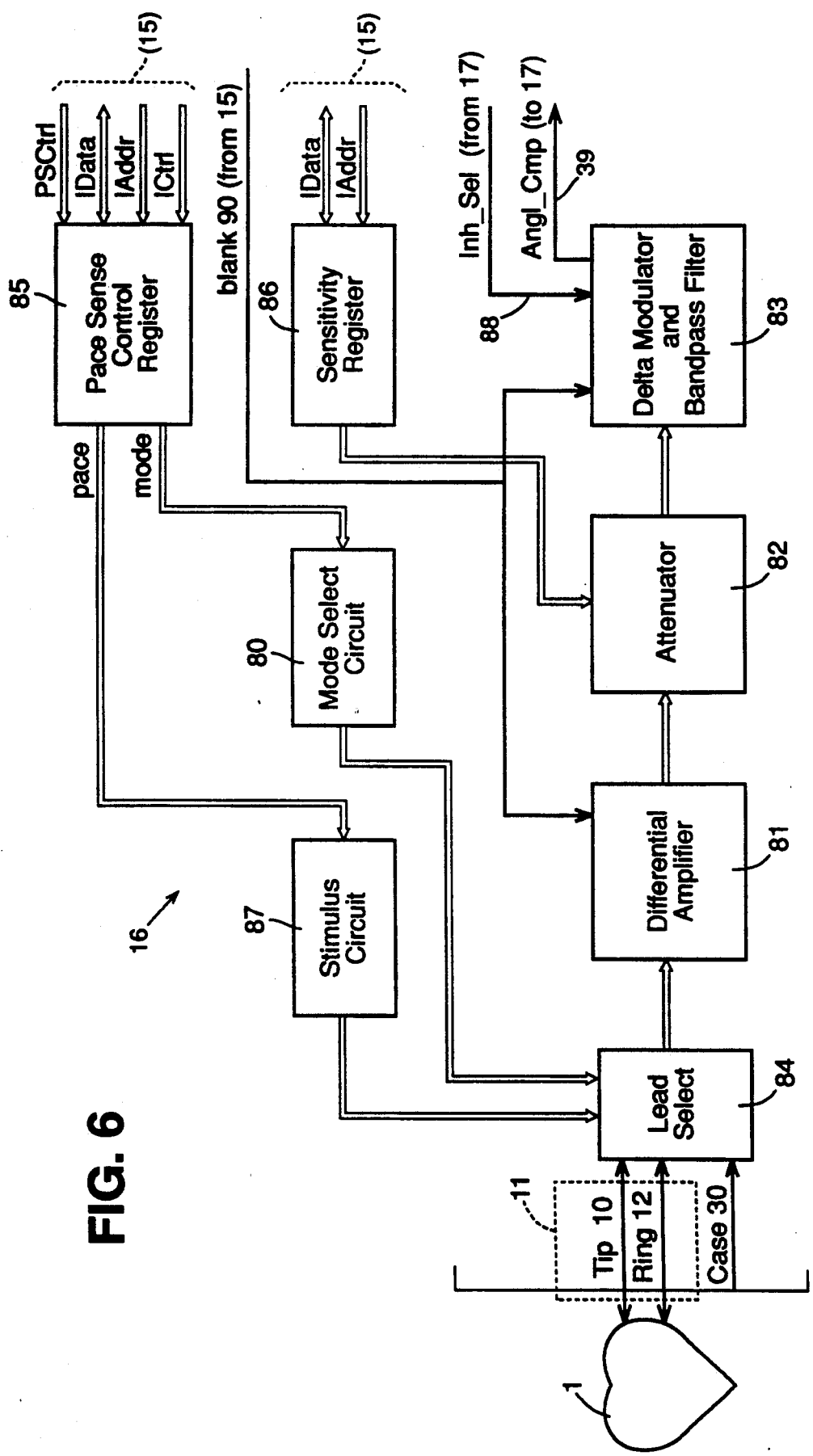
FIG. 6 is a high level block diagram which illustrates the functional block elements of a pace/sense analog circuit, one of the components of the implantable cardiac stimulation device shown in FIG. 2.

FIG. 6 is a high level block diagram, which illustrates the functional block elements of the pace/sense analog circuit 16. The pace/sense analog circuit 16 delivers voltage pulses to the heart via lead 11, and it converts sensed signals on the lead 11 to an amplified, filtered and delta-modulated digital signal stream. The pace/sense analog circuit 16 may generate voltage pulses for different purposes, such as stimulation or artifact compensation. The controller 28 (FIG. 2) may program the pace/sense analog circuit 16 to perform unipolar (tip 10 to case 30) or bipolar (tip 10 to ring 12) pacing modes. The controller 28 may also program the pace/sense analog circuit 16 to select unipolar or bipolar sensing modes, independent of the pacing mode. The pace/sense analog circuit receives control signals from the interface controller 15 (FIG. 2) and the intracardiac electrogram acquisition circuit 17 (FIG. 2) in addition to control signals from the controller 28.

The controller 28 may request the pace/sense analog circuit 16 to perform a pacing stimulus by writing command codes to the memory-mapped DAPS register of interface controller 15 via line 33 of FIG. 3. The interface controller 15 then generates signals on PSCtrl lines to the pace/sense control block 85, causing block 85 to create a pace signal to a stimulus circuit 87. The simulus circuit 87 responds by generating electrical pulses to a lead select block 84, which relays these pulses to the heart via the lead 11. The pace signal informs the stimulus circuit 87 how to select the correct polarity of signals and the durations of signals of a particular polarity. The controller 28 determines the lead configuration of pacing and sensing by writing to a memory-wrapped register, called PS Control (not shown), within the pace/sense control block as, via lines IData and Iaddr, causing block 85 to create a mode signal to a mode select circuit 80. The mode select circuit 80 then generates configuration signals and applies them to the lead select block 84, which employs switches to appropriately connect the tip electrode 10 and ring electrode 12 to the pace/sense analog 16 circuits in unipolar and bipolar modes of operation. Further, the controller 28 determines the sensitivity level for cardiac electrical signal sensing by writing to a memory-mapped sensitivity register (not shown), within the sensitivity block 86 via lines IData and Iaddr, causing block 86 to set control lines within an attenuator circuit 82, the operation of which will be discussed hereinafter.

Figure 14:
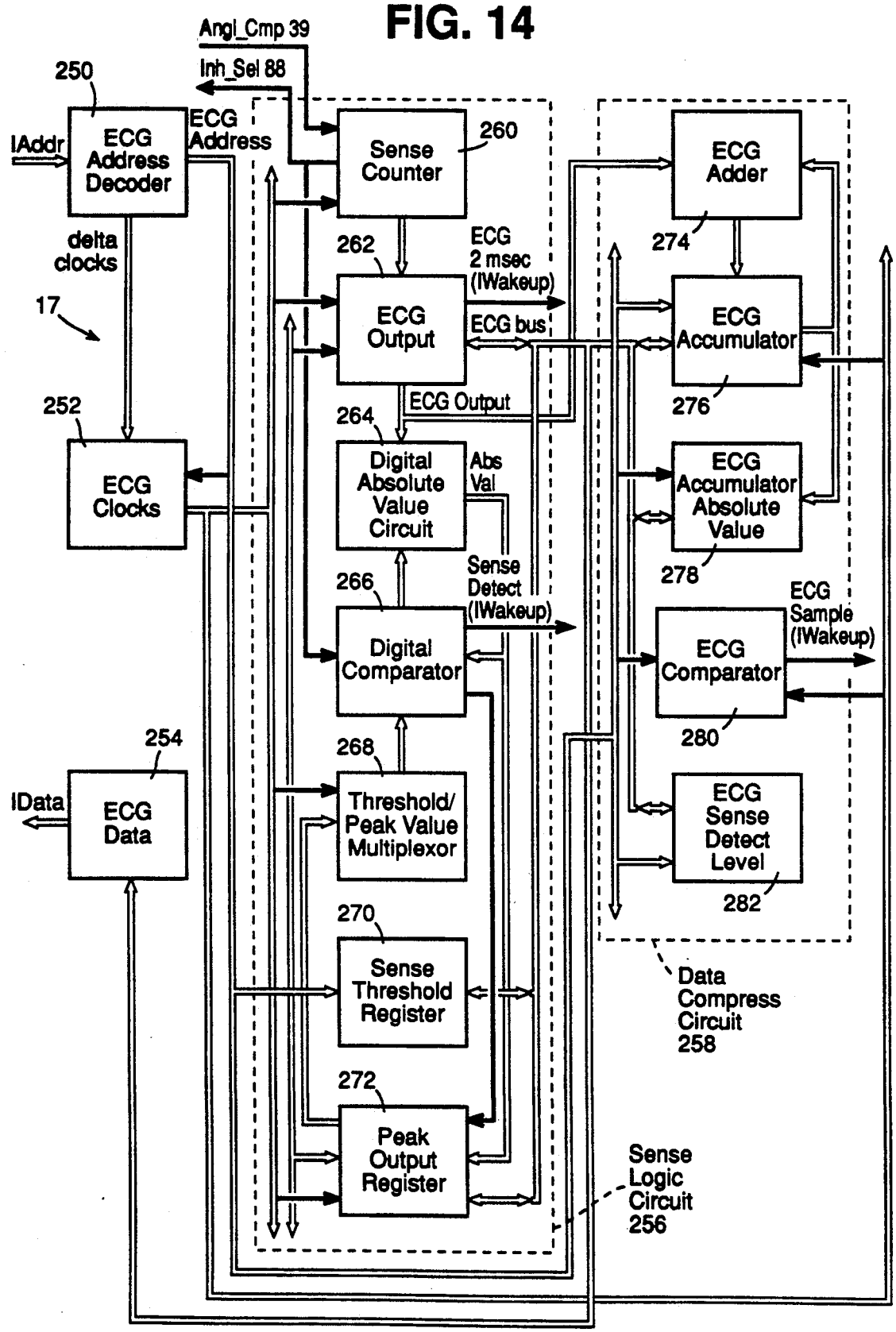
FIG. 14 is a high level block diagram which illustrates the functional block elements of an intracardiac electrogram acquisition circuit block, one of the components of the implantable cardiac stimulation device shown in FIG. 2.

The pace/sense analog circuit 16 senses electrical signals from the lead 11 and performs delta modulation of these signals to produce a continuous, 1 bit wide, bit-stream of data, Angl_Cmp, which is then input to the intracardiac electrogram acquisition circuit 17, depicted in the block diagram of FIG. 14. The intracardiac electrogram acquisition circuit 17 includes a sense counter 260, which converts this bit stream of data to digital samples at 500 Hz, an ecg output register 262, that provides access to the six-bit 2 msec data from the counter to other circuit blocks within the electrogram acquisition circuit 17, a digital absolute value circuit 264, that takes the absolute value of the data and a digital comparator 266, which compares the data Abs Val with an adjustable digital threshold, which is set by the controller 28 by a write operation to a sense threshold register 270. (Note that timing control for the various circuits of the electrogram acquisition circuit 17 are provided by an ECG clocks circuit 252). If the signal is greater than the threshold, the digital comparator 266 of the intracardiac electrogram acquisition circuit 17 produces a wakeup signal sense detect for detection by the controller 28 if the sense wakeup is not masked. The intracardiac electrogram signal, sensed from either or both the atria or ventricles, is one of the signals which may be sensed by the cardiac stimulation device 110 and sent to the external monitoring device computer system 100 of FIG. 1 for display. The digital comparator 266, in addition to continuously comparing the data Abs Val to the sense threshold register 270, also compares the data Abs Val to a peak output register 272. If Abs Val is greater than the peak output register 272, a threshold-/peak value multiplexor 268 circuit writes the value of Abs Val to the peak output register 272. The controller 28 may read and use the peak output register 272 value. Such a read operation by the controller 28 automatically resets the peak output register 272 to zero.

Referring again to FIG. 6, the pace/sense analog circuit 16 is a combination of six elements: a mode select circuit 80, a differential amplifier 81, an attenuator 82 to provide gain control, a combined bandpass filter and delta modulator 83, a lead select block 84 and a pace/-sense control register 85, which perform the sensing operation. In general, referring to FIGS. 1 and 2 in conjunction with FIG. 6, commands from the external monitoring device computer system 100 are sent to the cardiac stimulation device 110, which determine the content of commands set by the controller 28 to registers (not shown) within the pace/sense control register 85. These registers are discussed in this section.

The signal on the lead 11 is input via lead select block 84 to the differential amplifier 81, which amplifies and filters the signal. An input coupling amplifier (not shown) in the differential amplifier 81 circuit is selected to provide filtering of signals below a highpass corner frequency ranging from 10 to 16 Hz. A highpass corner frequency of 16 Hz is ideal for electrocardiogram sensing. A highpass corner frequency below 16 Hz passes more pacing artifact and unwanted T-wave sensing (from cardiac repolarization). A highpass corner frequency above 16 Hz attenuates desirable cardiac signals. A highpass corner select bit in a register in the pace/sense control block 85 may be written by the controller 28 to select a different highpass corner. The highpass corner select bit determines whether to switch an additional coupling capacitor (not shown) into the differential amplifier 81 circuit, which causes the highpass corner frequency to switch to about 2 Hz. By setting the highpass corner frequency to 2 Hz, the bandpass filter within the delta modulator and bandpass filter block 83 may be set to allow the pace/sense analog circuit 16 to sense lower frequency cardiac signals including evoked potentials. The operation of the delta modulator and bandpass filter block 83 is described in detail in U.S. Pat. No. 4,692,719, entitled "Combined Delta Modulator and Bandpass Filter", which issued to R. H. Whigham on Sep. 8, 1987.

The signal from the differential amplifier 81 is input to the attenuator 82. The controller 28 writes to an 8-bit memory-mapped register, called sensitivity register 86, to select the sensitivity setting for detecting intracardiac electrogram signals. The sensitivity register controls the attenuator 82 to program sensitivities from 0.3 mV to 13 mV by setting each of eight switches within a resistor network circuit (not shown) to an open or closed condition.

The analog signal from the attenuator 82 then passes to the combined bandpass filter and delta modulator 83 which outputs a 1-bit wide bit stream, called Angl_Cmp, on line 39, at a rate of 32 kbaud. Referring, again to FIG. 14, a signal Inh_Sel on line 88 from the intracardiac electrogram acquisition circuit 17 interrupts this bit stream every 2 ms (for two clock cycles out of 64) to read the digital signal. Only 62 counts out of 64 are read so that a signal accumulated by the sense counter 260 within the intracardiac electrogram acquisition circuit 17 will fit into a 6-bit ±31 count value. During the other two clock cycles, the intracardiac electrogram acquisition circuit 17 updates various internal circuit elements. The controller 28 may also command an interruption of the bit stream by codes written to a register in the pace/sense control block 85 to provide for power conservation, for example, during refractory periods of the heart when no cardiac signal is present to be sensed.

The intracardiac electrogram acquisition circuit 17 monitors the signal stream Angl_Cmp from the pace/sense analog circuit 16 to produce a digital data sequence of filtered and amplified electrocardiogram signals. The intracardiac electrogram acquisition circuit 17 controls and generates wakeup signals ECG 2 msec, ECG sample and Sense Detect to activate firmware-programmed procedures in the controller 28 and loads digital data samples into digital registers, the ECG output register 262, the sense threshold register 270, the peak output register 272 and an ECG accumulator register 276, to encode electrocardiogram data for the controller 28 to read. An ECG address decoder 250 provides addressing control signals for the electrogram acquisition circuit 17 which enables the controller 28 to access these registers. An ECG data buffer 254 provides for access between the controller 28 and these registers. The ECG accumulator register 276 has a capacity of nine-bits and receives data from an ECG adder 274, that continuously adds the six-bit 2-msec samples from ECG output register 262. The ECG accumulator register 276 is automatically zeroed whenever it is read by the controller 28.

The controller 28 may read ECG data in more than one manner. In a first manner of operation, the controller 28 reads the data at regular timed intervals to reconstruct a cardiac signal. In this manner of operation, the controller 28 must read the ECG accumulator register 276 before eight ECG output register 262 samples have accumulated to assure that overflow has not occurred. In a second manner of operation, the ECG accumulator register 276 may instead continuously accumulate the signal and notify the controller 28 when the ECG accumulator register 276 has overflowed. To operate in this second manner, the controller 28 must enable an ECG sample wakeup. An ECG accumulator absolute value circuit 278 rectifies the 9-bit data from the ECG accumulator register 276 and passes the resulting absolute value signal to an ECG comparator 280. A memory-mapped ECG sense detect level register 282 may be initialized by write operations by the controller 28. When the ECG comparator 280 determines that the data value in the ECG sense detect level register 282 is less than the ECG accumulator absolute value circuit 278 value, the ECG comparator 280 generates a wakeup signal, ECG sample. The digital signal which encodes electrocardiogram data may be used for analysis by the controller 28 or for transmission to an external programming device via the telemetry block 26.

The intracardiac electrogram acquisition circuit 17 provides for monitoring of the data by providing signals in two forms, wakeup signals to activate firmware-programmed procedures in the controller 28 and in the digital registers ECG output 262, ECG accumulator 276 and peak output 272, which encode the intracardiac electrogram data. The intracardiac electrogram acquisition circuit 17 monitors a signal stream from the pace/sense analog circuit 16 to produce the aforementioned 6-bit, 500 Hz digital data sequence of filtered and amplified electrocardiogram signal. The Angl_Cmp signal on line 39, the 1-bit wide bit stream from the pace/sense analog circuit 16, is input to the intracardiac electrogram acquisition circuit 17, which sums the counts in the bit stream over a 2 ms interval in a sense counter 260. The bit stream signal is a two level waveform representing the sensed signal as a sequence of bits indicating the time history of increases and decreases in the signal amplitude on the lead 11. The intracardiac electrogram acquisition circuit 17 resets the counter to a digital value of −31 at the beginning of each 2 ms period, reads the counter at the end of 62 clock cycles and stores this digital data sample value, in the range from ±31 in the ECG output register 262. The least significant five bits of ecg data encode the magnitude of the data sample value. The sixth bit of ecg data encodes the sign of the data. Bits 7 and 8 are always zero. Since the digital data in ecg output register 262 remains unchanged for only 2 ms, an additional data accumulator is necessary to allow the controller 28 to monitor the signal less frequently.

The ECG accumulator 276 is a 9-bit register which allows the accumulation of electrocardiogram data for 12 ms without overflowing. The intracardiac electrogram acquisition circuit 17 automatically initializes the ECG accumulator register 276 to zero after each time the controller 28 reads the register. Since the controller 28 operates only on 8-bit data bytes, ECG accumulator register 276 is read and written as two bytes. The controller 28 must read the register containing the least significant 8 bits of ECG accumulator register 276 prior to reading the register containing the most significant bit.

The peak output register 272 is an 8-bit register which stores the peak value of ECG output register 262, the largest magnitude of the least significant five bits of ECG output register 262 which has occurred since its last reading by the controller 28. If this peak magnitude is negative in sign, the sign bit is set to one in bit seven of peak output register 272.

The intracardiac electrogram acquisition circuit 17, under direction of instructions set forth by the controller 28 in codes written to the aforementioned memory-mapped registers, sense threshold register 270 and ECG sense detect level register 292 within the intracardiac electrogram acquisition circuit 17, generates up to three different wakeup signals. One wakeup signal is sense detect. The controller 28 sets a programmable threshold level by writing to the 8-bit memory-mapped register, sense threshold register 270. If digital electrocardiogram data signals exceed the value of sense threshold register 270, then the intracardiac electrogram acquisition circuit 17 generates the sense detect wakeup.

A second wakeup signal is a compressed electrocardiogram wakeup ECG sample which, if enabled, generates a wakeup signal when a digital electrocardiogram data signal exceeds the value in the memory-mapped register ECG sense detect level 282. The controller 28 sets this programmable threshold level by writing a 4-bit value to ECG sense detect level register 282. The intracardiac electrogram circuit asserts an ECG sample wakeup whenever the absolute value of the digital value in register 276 exceeds the value in the ECG sense detect level register 282.

A third wakeup signal is an electrocardiogram synchronization wakeup which, if enabled, generates an ECG 2 msec wakeup signal every 2 ms, immediately after the intracardiac electrogram acquisition circuit 17 stores a new electrocardiogram sample value in ECG output register 262. The controller 28 may enable or disable each of the sense detect, ECG 2 msec and ECG sample signals by writing a corresponding bit in a wakeup mask register.

Figure 7:
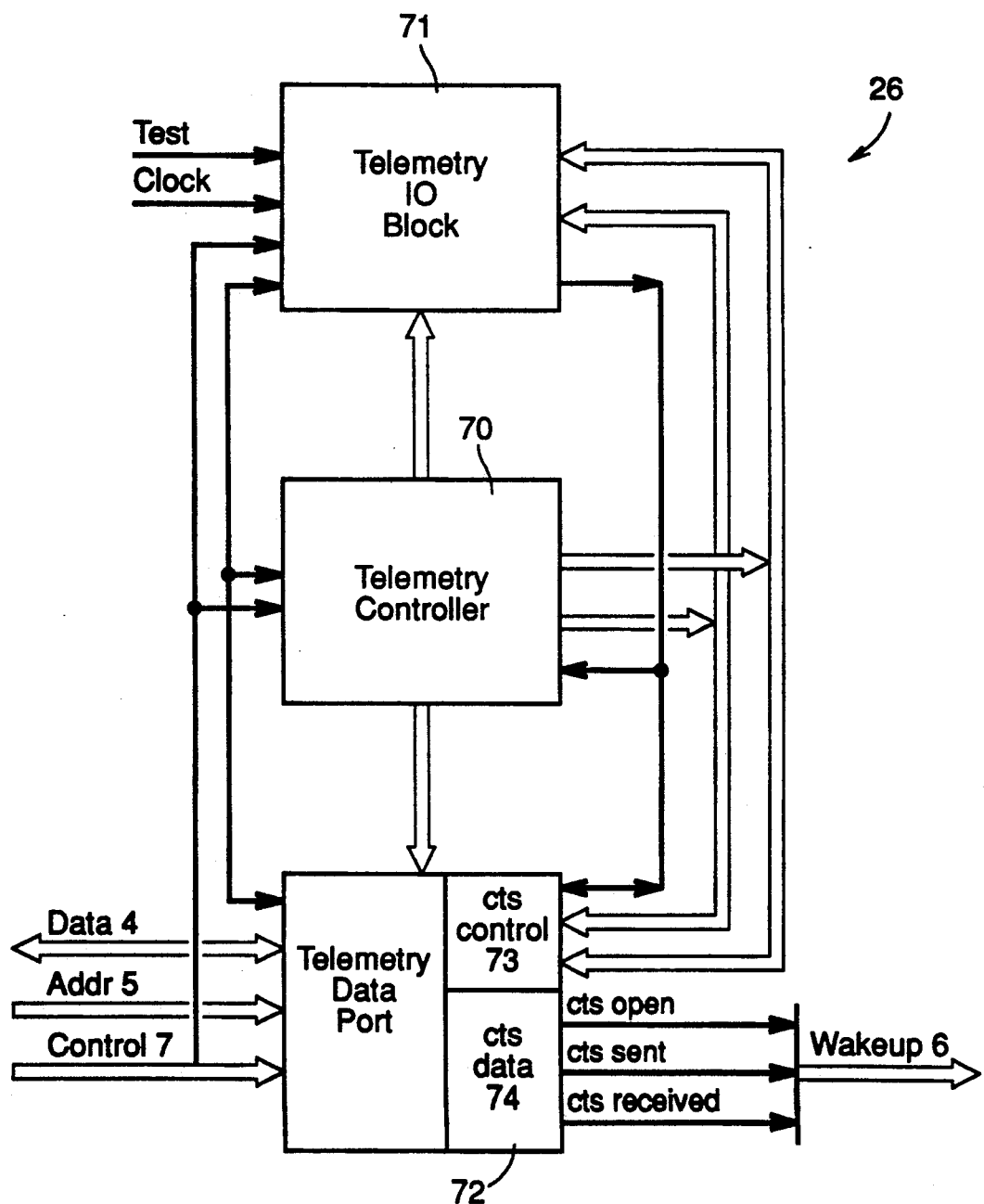
FIG. 7 is a high level block diagram which illustrates the functional block elements of a telemetry block, one of the components of the implantable cardiac stimulation device shown in FIG. 2.

FIG. 7 is a high level block diagram which illustrates the functional block elements of the telemetry block 26. Internally, the telemetry block 26 communicates with the controller 28 (FIG. 2) by means of two 8-bit memory-mapped interface registers, cts control register 73 and cts data register 74, and three wakeup request signals, CTS Open, CTS Sent and CTS Received of Wakeup lines 6. When communication is active, the telemetry block 26 requires 32 kHz clock signals from fast clock 29 (FIG. 2), as discussed hereinafter, to provide internal timing events.

Telemetry block 26 comprises three subsystems: a telemetry controller 70, a telemetry input/output block 71 and a telemetry data port 72. The memory-wrapped registers cts control 73 and cts data 74 are components of the telemetry data port 72. The telemetry controller 70 is a control store firmware-based, control sequencer designed specifically for implantable applications. The telemetry input/output block 71 performs interfacing functions between the telemetry controller 70 and the controller 28. The telemetry input/output block 71 includes circuits which control the three wakeup request signals, CTS Open, CTS Sent and CTS Received of Wakeup lines 6. The controller 28 governs the operations of the telemetry controller 70 by writing commands to memory-mapped wakeup control registers, wakeup flag reset, wakeup flag set and wakeup mask signals, within a controller input/output block (not shown but residing within the controller 28). Each of the wakeup flag reset, wakeup flag set and wakeup mask registers within the controller input output block includes a control bit which corresponds to each of the CTS Open, CTS Sent and CTS Received signals of Wakeup lines 6. The telemetry data port 72 includes a shift register for transmitting data to an external device one bit at a time, the aforementioned control status register cts control, and a transmit and receive buffer which, in combination, comprise the aforementioned cts data register 74.

The controller 28 may read and write to the control status register, cts control register 78. Cts control register 73 includes six status and/or control bits. The controller 28 writes a transmission mode control bit to determine the mode of data transmission from the implantable cardiac stimulation device 110 to the external programmer. In one transmission mode, the telemetry block 26 sends eight bits of data every eight milliseconds. Otherwise, the telemetry block 26 sends six bits of data every four milliseconds.

One status bit of the cts control register 73 indicates when the transmit buffer is empty and, therefore, another data byte may be sent to an external device. Another status bit indicates when the receive buffer is full and, therefore, the controller 28 may read a data byte which has been transmitted to the implanted cardiac stimulation device 110. A third status bit designates when the transmission channel between the implantable and external devices is no longer performing a communication operation.

The controller 28 reads and writes data to the external device by reading and writing data bytes to the cts data register 74.

A communication task is a routine performed by firmware within the cardiac stimulation device 110 in response to a single command from an external monitoring device computer system 100. Each task is initiated when the computer system 100 sends a command word to the cardiac stimulation device 110. Command word contents designate the type of communication to be performed (e.g. reading data from the system into the device, writing data from the device into the system, sending physiological data from the device to the system or requesting the device to perform an operation), the location within the cardiac stimulation device 110 to read or write, and any required control information.

Figure 8:
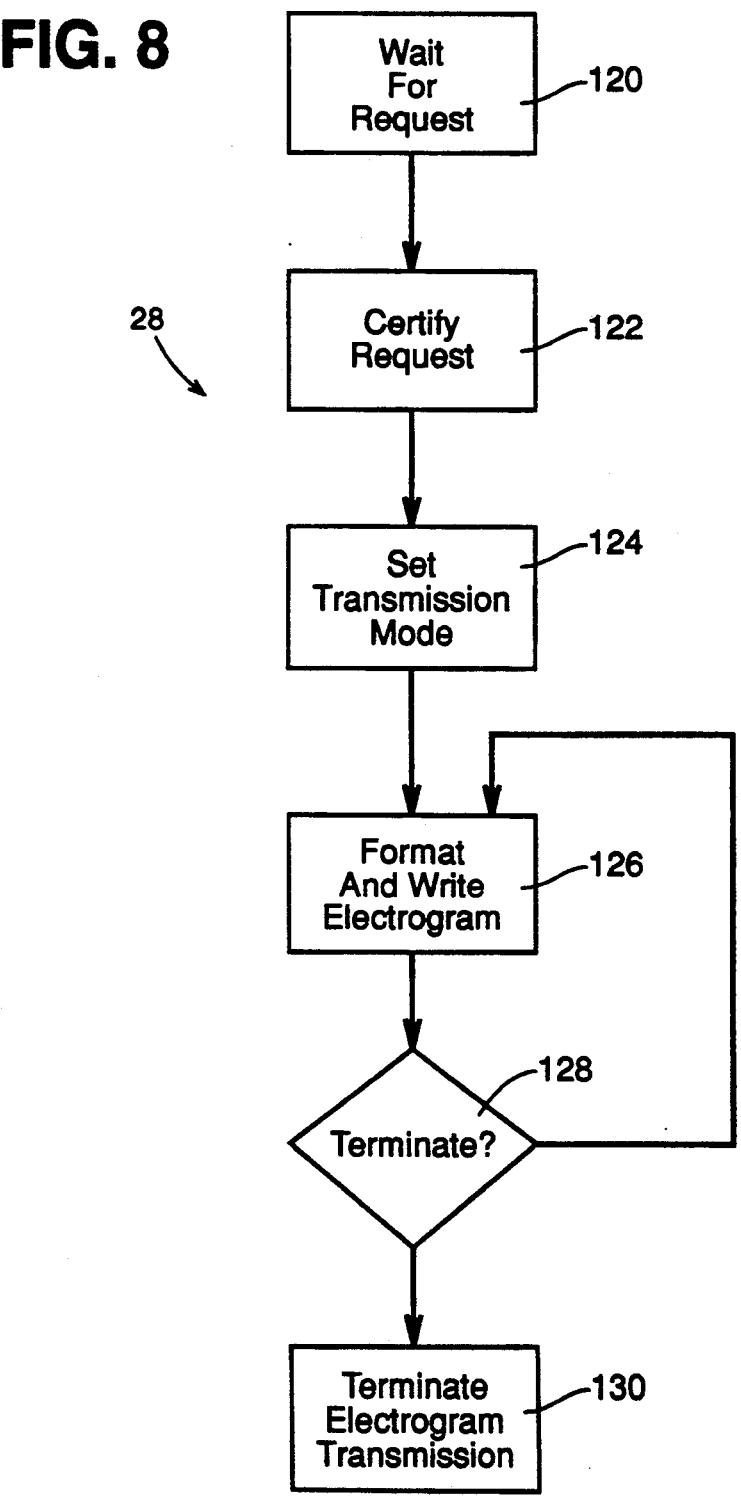
FIG. 8 is a flow chart which describes operations for transmitting intracardiac electrogram and other physiological signal data to an external monitoring device computer system.

FIG. 8 describes the operations performed by the controller 28 firmware to transmit intracardiac electrogram and other physiological signal data to an external monitoring device computer system 100. In wait-for-request block 120, the cardiac stimulation device 110 waits for an intracardiac electrogram request from the computer system 100. A command from an external monitoring device computer system 100 requesting intracardiac electrogram or timing event transmission initiates transmission from the cardiac stimulation device 110 to the computer system 100 of intracardiac electrogram data and 0, 1, or 2 channels of main timing event mte information. Main timing events mte are physiological events or data which are detected or measured by the cardiac stimulation device. Mtes include sensed cardiac events such as P waves, R waves and noise signals. The cardiac stimulation device of the present invention also includes sensor measurements, particularly impedance measurements (sensor measurement result on line 22 of FIG. 3), as mte data. The controller 28 continuously detects and measures physiological signals as it performs its control functions. When events are detected or measured, the controller 28 stores event codes or measured data in memory locations called "mte buffers". The controller 28 may transmit this information to an external monitoring device 100 according to the procedures described hereinafter.

Referring to FIG. 8 in conjunction with FIGS. 1 and 2, in certify-request block 122 controller 28 firmware checks for any data transmission or command mismatch errors in the request. If the request is valid, firmware sends a command acknowledge code to the external monitoring device computer system 100. At this time, firmware also clears each memory location containing sensor or event information to zero to allow the external monitoring computer system 100 to synchronize the data bit stream of the sensor and event information. The first asserted sensor or event bit received by the computer system 100 is the start bit signifying the beginning of the data.

In set-transmission-mode block 124, after the controller 28 firmware has acknowledged the command, firmware sets telemetry 26 hardware into six bit data transmission mode which establishes a communication protocol in which six bits of data are sent in 3.906 ms frames. Then, in format-and-write-electrogram block 126, firmware loads electrogram data from the ECG accumulator register 276 within the intracardiac electrogram acquisition circuit 17 of FIG. 2 and formats intracardiac electrogram (and mte, if requested) data into an eight bit word and provides it to telemetry block 26 hardware by writing it into cts data register 74 within telemetry block 26. In the six bit transmission mode, telemetry block 26 hardware sends the six most-significant bits and drops the least two, thus the bandwidth of the link is limited to six bit words, each sent at 3.906 ms intervals. Telemetry block 26 hardware generates a wakeup signal, cts sent, each time it successfully sends a word. Upon each of these wakeup events, firmware accesses, formats and sends another word. According to terminate block 128, firmware continues to loop on format-and-write-electrogram block 126 until either the communication link breaks or the external monitoring device computer system 100 transmits data to the cardiac stimulation device 110. Note that the command which initiates transmission does not specify the duration of transfer. The firmware routine does not calculate or transmit a data checksum for ecg data transmission. When the data transmission task ends, the controller 28 sets telemetry 26 hardware to 8-bit mode in terminate-electrogram-transmission block 130.

Thus, firmware's job is to take data from ecg and mte buffers and format it for telemetry 26 hardware. Any of the firmware routines for controlling the cardiac stimulation device 110 which derive a sensor measurement value or detect a pacing or sensing event may load an mte buffer with data upon the occurrence of either event. This data loading may take place whether or not transmission of data is enabled. The telemetry firmware routine empties the mte data buffer as fast as the telemetry link permits (one bit per 3.906 ms frame). If an event occurs and a loading event determines that an mte buffer it wishes to load is not empty, the loading event will skip the buffer loading step for that event to avoid "confusing" the system receiving the data. Thus, if possible the length of an mte data buffer should be chosen to be capable of complete transmission in the minimum time between events.

Commands from the external monitoring device computer system 100 determine the form the communication takes. There are three electrogram/mte processing routines in firmware, which format physiological data and event markers. An electrogram-only routine sends intracardiac electrogram data in all six bits of the word. It reads electrogram data from the ECG accumulator register 276 within the intracardiac electrogram acquisition circuit 17 (FIG. 2) and writes it directly into cts data register 74 within telemetry block 26 (FIG. 2). An electrogram-sensor routine sends the four most significant bits of parallel electrogram data in bits<5:2> of the word, pace/sense event markers (denoting sensed cardiac events, generated pulses, for example) as serial data in bit<1>, and sensor information (for example, respiration signals from an impedance sensor) as serial data in bit<0>. An electrogram-event routine sends the five most significant bits of parallel electrogram data in bits<5:1> of the six-bit word and sends serial pacing and sensing event information which is stored in controller 28 memory in bit<0>.

Figure 9:
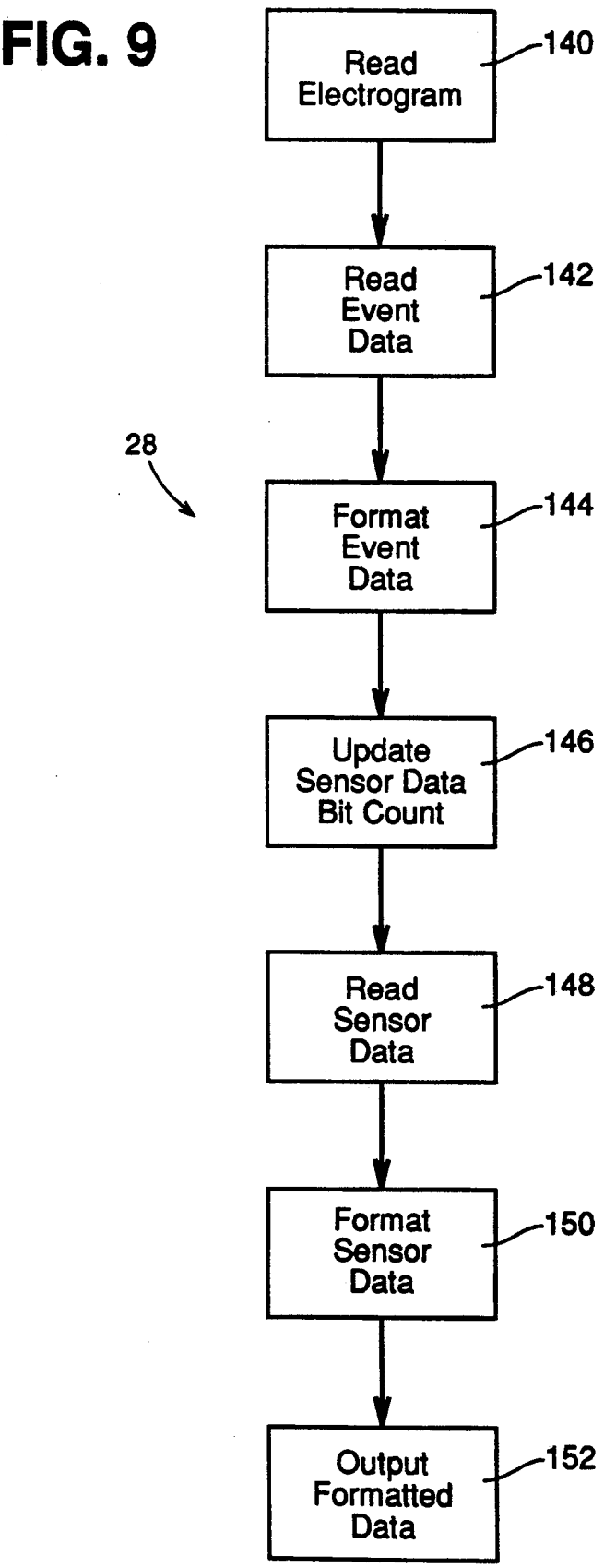
FIG. 9 is a flow chart which describes the operations for formatting intracardiac electrogram and sensor data for transmission to an external monitoring device computer system.

FIG. 9 describes the operations performed by the controller 28 firmware to format intracardiac electrogram and sensor data for transmission to the external monitoring device computer system 100. Referring to FIG. 9 in conjunction with FIGS. 1-3, in read-electrogram block 140 controller 28 firmware reads electrogram data from the ECG accumulator register 276 in the intracardiac electrogram acquisition circuit 17 and saves it in a temporary memory location "temp" (not shown). In read-event-data block 142, firmware reads pace/sense event data from byte zero of an mte buffer holding sensor information (from the sensor measurement result register, via line 22 of FIG. 3) within the controller 28 memory. Byte zero of this mte buffer may hold a code which signifies the occurrence of an event such as an atrial pace event, an intrinsic atrial heartbeat event (a P-wave), a ventricular pace event, an intrinsic ventricular heartbeat event (an R-wave) or another predefined event. Next, in format-event-data block 144, firmware shifts the sensor measurement data right, replaces the data within the same memory location and sets bit<3> of the temporary memory location "temp" to the result of the carry status following the aforementioned right shift operation. Next, update-sensor-data-bit-count block 146 reads byte one of the sensor mte buffer in controller 28 memory. Byte one of the sensor mte buffer holds the sensor data bit count which defines the amount of sensor data currently held in the sensor mte buffer. If the bit count is zero, bytes two and three of the sensor mte buffer memory are empty and no sensor data is available for transmission. In this case, firmware sets bit<2> of the temporary memory location "temp" to 0. If the bit count is not zero, firmware decrements the count and stores it back in byte one of the mte sensor buffer memory, divides the bit count by 8 to give the byte count, and employs the byte count as a pointer for addressing higher order bytes of the mte sensor buffer (e.g. byte two or byte three, although other embodiments of the invention may employ additional bytes).

Next, in read-sensor-data block 148, firmware reads sensor data from controller 28 memory which holds an appropriate physiological sensor value. An example of such a sensor measurement is the minute volume value derived in the sampler block 48 of FIG. 5. The preferred embodiment of the invention transmits the minute volume value to indicate the patient's metabolic demand. In addition to formatting the sensor measurement, upon deriving a new pacing rate in summer block 58 of FIG. 5, the new rate may be encoded and stored in the sensor data memory buffer for transmission. Furthermore, firmware may also encode and store data from the sampler block 48, the short-term averager 50 and the long-term averager 52 of FIG. 5 to allow analysis of the respiratory tidal volume signal, the short-term average and the long-term average respiration signals.

Next, in format-sensor-data block 150, firmware formats respiration signal data for transmission. In one embodiment, firmware shifts the sensor measurement data right, replaces the data within the same memory location and sets bit<2> of the temporary memory location "temp" to the result of the carry status following the aforementioned right shift operation. In the preferred embodiment of the invention, better dynamic range for the transmitted signal is provided by determining the change, or delta value, of the current measurement result in comparison to the most recent measurement result. Therefore, firmware formats the respiration signal data by subtracting the previously stored measurement result from the current measurement result to determine the delta value. Firmware then stores the current measurement value in the memory location previously holding the most recent measurement value. Firmware then shifts the delta value right, replaces the data within the same memory location and sets bit<2> of the temporary memory location "temp" to the result of the carry status following the aforementioned right shift operation. Note that the sampler block 48 of FIG. 5 may write the data into the sensor memory buffer for each sensed sample, for example at 100 ms sensor intervals. Then, the data transmission firmware performs this shifting and replacing operation, for example at approximately 4 ms bit intervals. Thus, the data transmission firmware can format as many bits of sensor information as can be transmitted in a sensor interval. In this example, 18 bits of sensor data can be transmitted within the sensor interval to allow for a start bit ("1") and an end bit ("0"). Finally, in output-formatted-data block 152, firmware writes the temporary memory location "temp" to the cts data register 74 for transmission to the external monitoring computer system 100.

Telemetry 26 hardware produces an intracardiac electrogram having a value ranging from −31 to +31 each 1.953 ms (nominally, 2 ms), which it accumulates into 9-bit ECG accumulator register 276. When the controller 28 reads this register, intracardiac electrogram acquisition circuit 17 hardware thereafter automatically zeros the ECG accumulator register 276. During telemetric transmission of intracardiac electrogram data, firmware transmits one 6-bit word every 3.906 ms (nominally, 4 ms). A standard firmware execution latency, which may delay a reading of the ECG accumulator register 276, may last 1.2 ms. Due to this latency, the register 276 may accumulate up to three of the 1.936 ms data samples to produce a value ranging from −93 to +93. Given this range of values, no data is lost by reading only the lower eight bits of the ECG accumulator register 276. Telemetric transmission provides for sending 6, 5 or 4 bits of the ECG accumulator register 276 information every 4 ms depending, respectively, on whether intracardiac electrograms are transmitted alone, including event information, or including both event information, and sensor data. The communications firmware ignores the ninth bit of the ECG accumulator register 276, which is appropriate since its value is always zero because data is transmitted every 4 ms.

In the previous description, note that data transmission firmware truncates the lower 2, 3 or 4 bits of the ECG accumulator register 276. (Two bits are truncated on a direct write from the 8-bits of the ECG accumulator register 276 to the transmitted six bits of the cts data register 74.) Truncation of the lower order data bits leads to mild to extreme levels of distortion of the intracardiac electrogram waveform. This can be attributed to the nonlinear effects of truncation of delta modulator information. Truncation of delta modulator bits has a much more marked effect on the recreated ECG than general truncation of the waveform itself (quantization).

Figure 10:
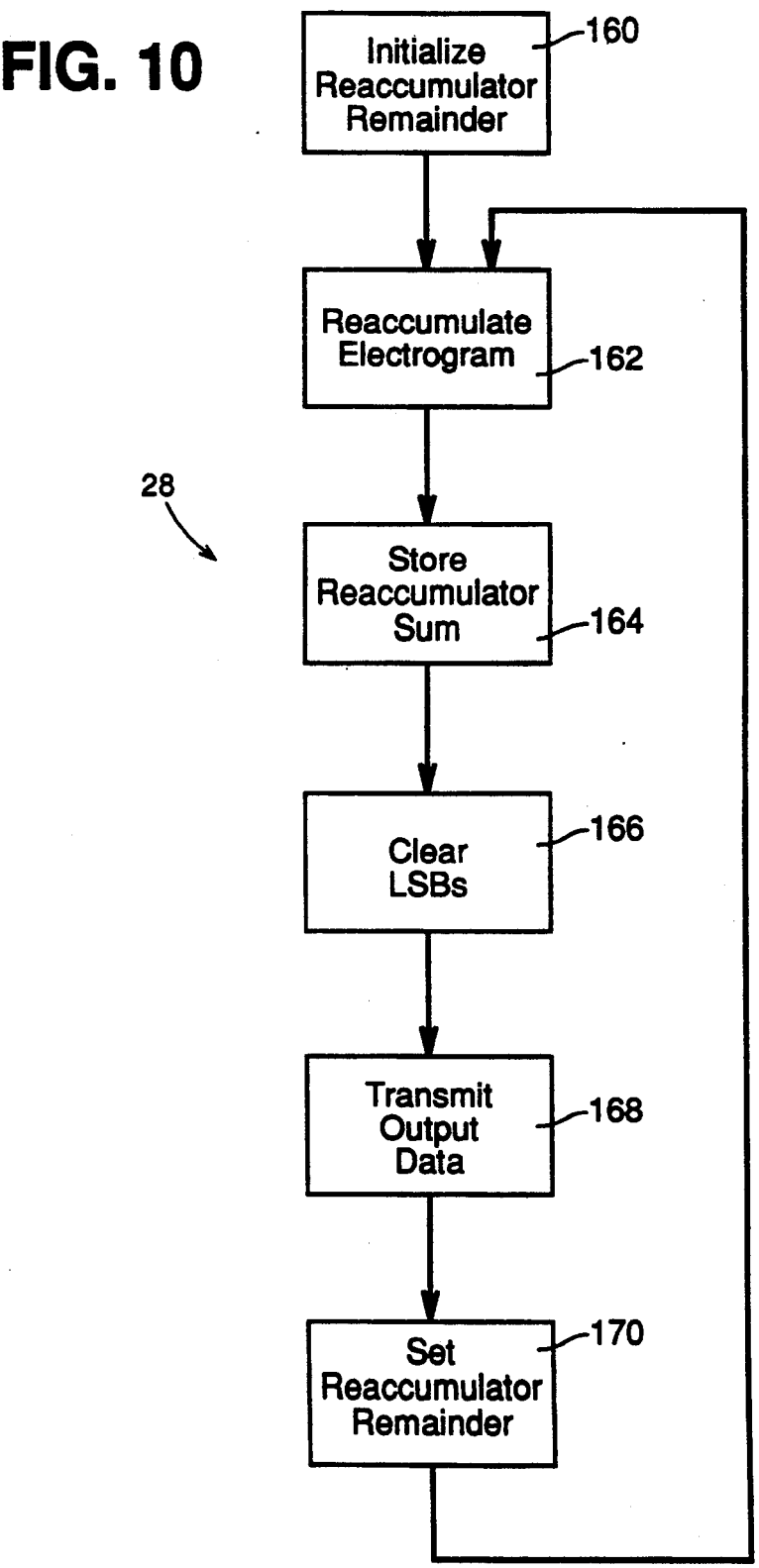
FIG. 10 is a flow chart which illustrates steps for reaccumulating truncated data.

FIG. 10 is a flow chart which illustrates steps for reaccumulating truncated data. Reaccumulation of truncated data bits requires addition of a previous sample's truncated bits onto the next sample. The reaccumulation procedure takes place in conjunction with the procedure for transmitting intracardiac electrogram and other physiological signal data shown in FIG. 8. Initialize-reaccumulator-remainder 160 is the first step in the reaccumulation procedure. This step initially sets a word in controller 28 memory, called reaccumulator remainder, to zero. The reaccumulator remainder is updated during subsequent loops of the reaccumulation procedure, as described below. Initialize-reaccumulator-memory 160 must take place prior to electrogram sampling and transmission, for example, in conjunction with the set-transmission-mode block 124 step of FIG. 8. All other steps of the reaccumulation procedure of FIG. 10 take place during the sampling and transmission of data in the format-and-write-electrogram block 126 of FIG. 8. In load-electrogram-sample step 162, firmware reads electrogram data from the ECG accumulator register 276 of the intracardiac electrogram acquisition circuit 17 of FIG. 2. Firmware then adds the current value of reaccumulator remainder to the electrogram data value stored in reaccumulate-electrogram step 162 and, in store-reaccumulator-sum step 164, stores the sum in a word in controller 28 memory, called reaccumulator sum. Firmware then determines an output data value by clearing the low order (least significant) bits of the reaccumulator sum data value in clear-LSBs step 166. Here, the two least significant bits are always cleared since telemetry 26 hardware only transmits the most significant six bits of an eight bit word written to the cts data register 74 while operating in the 6-bit, 4 ms data transmission mode. If any data bits are used to transmit sensor or event information, additional bits are cleared. Firmware then transmits the output data in transmit-output-data step 168 by writing the output data value to the cts data register 74. In set-reaccumulator-remainder step 170, firmware subtracts the output data value from the stored reaccumulator sum value and stores the result in the reaccumulator remainder memory word. On the next sample acquisition, the procedure loops back to load-electrogram-sample step 162 to continuously reaccumulate the truncated data until either the communication link breaks or the external monitoring device computer system 100 transmits data to the cardiac stimulation device 110.

Figure 11:
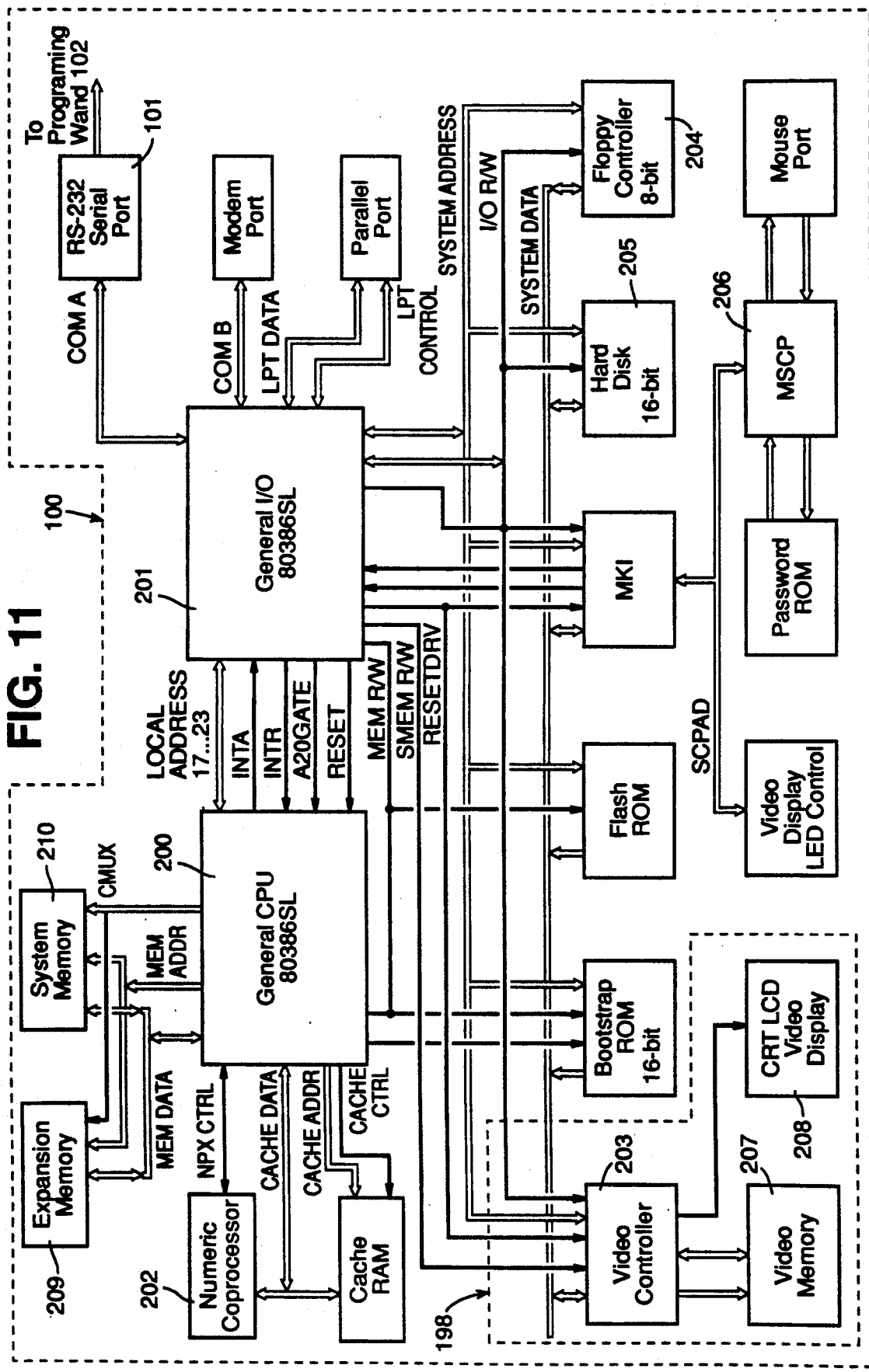
FIG. 11 is a functional block diagram of an external monitoring device computer system, a component of the present invention shown in FIG. 1.

FIG. 11 is a functional block diagram of the preferred embodiment of the external monitoring device computer system 100, which employs a commercially available notebook computer system such as the Zenith Data Systems MastersPort 386SX ®, Zenith Data Systems Corporation, St. Joseph, Mich. 49085. Although the block diagram of FIG. 11 includes numerous component blocks, only those blocks which are relevant to the functions and operations of the present invention are discussed individually. With regard to the present invention, and referring to FIGS. 1 and 2 in conjunction with FIG. 11, the computer system 100 displays the respiration or impedance data acquired by the cardiac stimulation device 110. In general, the computer system 100 allows an operator, such as a physician, to enable, control, monitor and document the functions and operations performed by the implantable cardiac stimulation device 110, and to monitor and document all data collected by the device 110. The controlling element of the computer system 100 is a general central processing unit or CPU 200, which drives all control and data manipulation operations performed by the computer system 100. The CPU 200 interfaces to a peripheral I/O controller 201, providing various communication and miscellaneous functional blocks (none of which are separately shown), including one or more programmable interrupt controllers, a programmable interval timer, two direct memory access (DMA) controllers, a parallel communication port, two serial communication ports, memory-refresh control logic, a real-time clock and a power management controller. An RS-232 serial port 101 supplies the function of transmitting control information and data to the implantable cardiac stimulation device 110, as well as the function of receiving data from the device. A numeric coprocessor 202 performs mathematical operations upon a request by the CPU 200. The CPU 200 provides control instructions to a VGA video controller 203, which drives a video display system 198. The computer system 100 also executes long-term data and program storage by means of a floppy drive controller 204 and a hard drive controller 205. A master system control processor or MSCP 206 is a microcontroller that combines normal keyboard processor functions and system control functions. The MSCP 206 provides keyboard serial code processing, a CPU reset, battery discharge rate monitoring and password protection, as well as other miscellaneous operations.

Software is employed to drive the external monitoring device computer system 100. Its primary function is to write control parameters and codes to the implantable cardiac stimulation device 110. Control parameters influence the operations, such as stimulation timing and amplitude, of the cardiac stimulation device 110. Control codes request the cardiac stimulation device 110 to perform a particular operation. Some of the control codes activate functional operations within the cardiac stimulation device 110, such as measuring, sampling, processing and communicating biological signals such as intracardiac electrograms, ultrasound waveforms, pressure signals and impedance signals. The external monitoring device computer system 100 accepts the information sent by the implantable cardiac stimulation device 110. The implantable cardiac stimulation device 110 can acquire data in real time and send this data, as it is acquired, to the computer system 100. This data may be in the form of intracardiac electrograms and physiological main timing events (MTEs). In the system of the present invention, other measurements, such as impedance signals that represent a respiration waveform, are formatted and sent from the implantable device 110 to the computer system 100 for display and analysis. The computer system 100, upon receiving data from the implantable device 110, may display the transmitted data, or other data derived from the transmitted data, in a graphic form, a numeric form or a combination of numeric and graphic forms.

In the preferred embodiment of the invention, software within the external monitoring device computer system 100 controls a display of up to three channels of graphics and one channel of event annotations, simultaneously in real time. Software may draw complete graphs and histograms. The graphic channels which may be displayed include intracardiac electrograms (which are sensed in either the atrium or the ventricle), surface electrocardiograms, ultrasound waveforms, pressure signals and impedance signals. Impedance signals may arise from physiological phenomena including respiration, cardiac contraction and body motion. Indicators of horizontal and vertical scale accompany graphic data displays, after calibration of the data.

The computer system 100 may display event markers with the intracardiac electrograms or other signal displays to characterize timing relationships between physiological events arising in the atria and ventricles of the heart in dual chamber and antiarrhythmia pacing devices. The external monitoring device computer system 100 receives event codes from the implantable cardiac stimulation device 110 and places markers on a display, possibly in combination with the display of electrocardiogram or other signal samples, in which such markers are annotated to indicate the type of cardiac event (e.g. sense, pace, noise) and, for appropriate markers, the chamber or location at which the event occurred. The computer system 100 may display critical time intervals such as refractory periods and blanking intervals in a manner which expresses the timing relationship of such events to cardiac events. The computer system 100 may display atrial and ventricular events in separate locations on a display screen, but the separate locations are shown in close enough proximity to demonstrate relationships between events in the two chambers. The computer system 100 marks events graphically to enable precise interval comparison and measurement.

Upon receiving information from the implantable cardiac stimulation device 110 via the RS-232 serial port 101 and formatting the data for display, the general CPU 200 of FIG. 11 accesses video display system 198 to generate a display on a graphics screen, discussed below. Software programs, which execute in the general CPU 200, display graphic information by writing control codes to the video display system 198. The video display system 198 consists of a video memory 207 having a capacity of 640×480 pixels, a CRT LCD video display 208 and video controller 203, which includes a number of I/O registers (not shown) and an arithmetic logic unit (ALU) with a barrel rotator (not shown). The CRT LCD video display 208 is a cold cathode fluorescent backlit black-on-white LCD screen, which displays 25 lines times 80 characters. In a VGA video mode, the CRT LCD video display 208 displays simulated color in 32 grey levels, 640×480 graphics resolution and 720×400 text resolution. The application of the present invention requires the usage of only a limited subset of I/O registers within the video controller 203. These registers (not shown) are graphics controller registers, in particular, a set/reset register, a data rotate register, a mode register, and a bit mask register.

Figure 12:
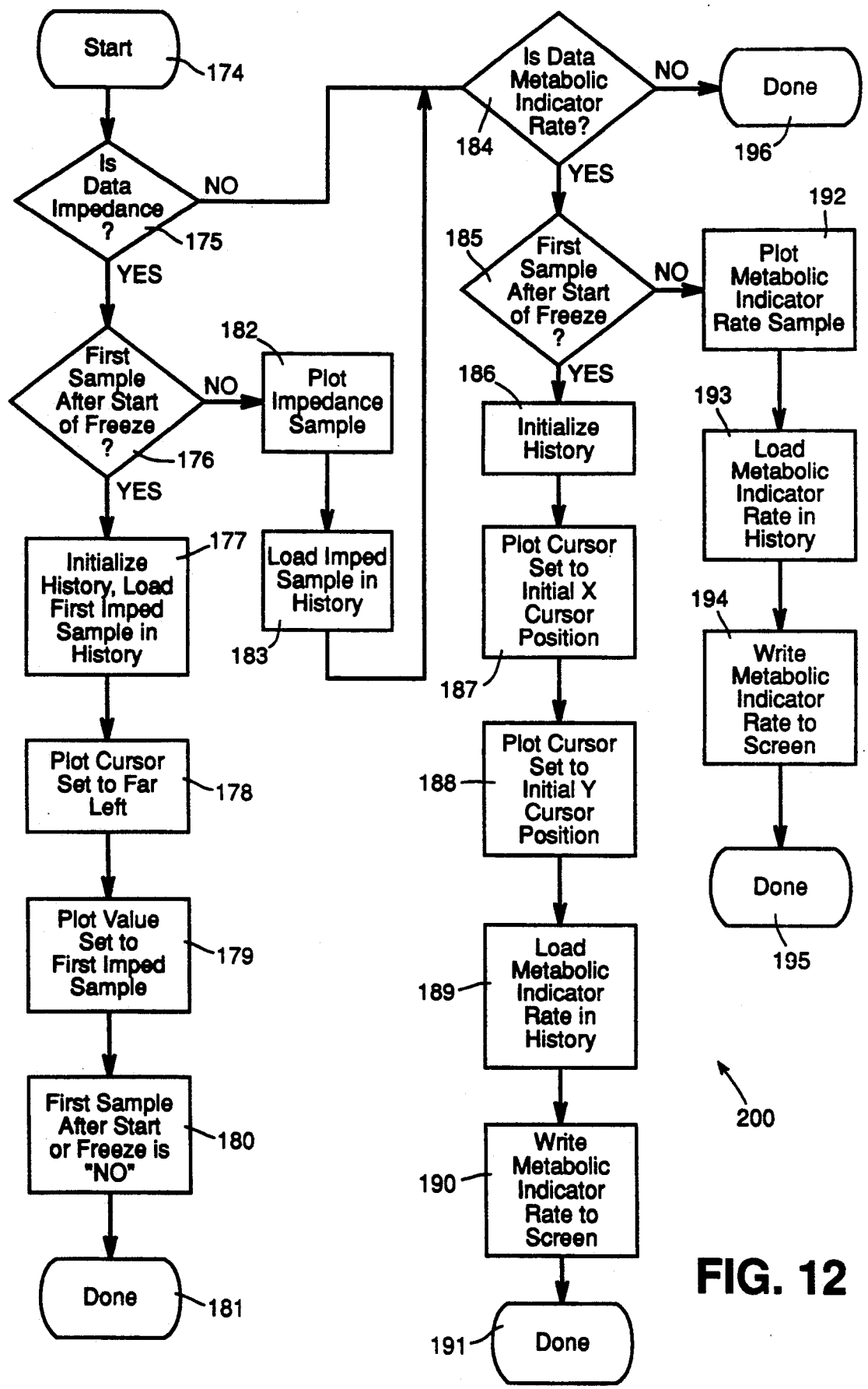
FIG. 12 is a flow chart which describes the operations performed by an external monitoring device computer system for displaying sensor data acquired by a cardiac stimulation device.

FIG. 12 describes the operations performed by the software of general CPU 200 (FIG. 11) to display within the external monitoring device computer system 100 sensor data acquired by the cardiac stimulation device 110. Software performs the operations of FIG. 12 each time the display screen 208 is updated (e.g. every 977 us). Asynchronously with respect to screen updating, the RS-232 serial port 101 receives sensor data from the cardiac stimulation device 110. Software running within the general CPU 200 acquires each bit of the serial bit stream of impedance data for a predetermined number of data transmissions from the cardiac stimulation device 110 via the RS-232 serial port 101. Recall that impedance signals from the cardiac stimulation device are sent, in the form of a serial bit stream, in the least significant bits of a six bit code which is transmitted approximately every 4 ms. The four most significant bits encode an intracardiac electrogram signal and bit<1> encodes cardiac event signals. The impedance signal is asynchronous with respect to cardiac signal events encoded by the intracardiac electrogram. Software assembles impedance data, either in the form of an impedance magnitude or an impedance delta value as previously described, by reading and shifting successive data bits. For the case in which delta values are transmitted, software adds the most recent value to the current delta value to determine the impedance signal magnitude. (For the first sample, in block 177, the most recent value is set to a predetermined value such as zero). Furthermore, software assembles metabolic indicator rate data similarly by receiving and shifting successive data bits (rate information is not normally transmitted in the form of delta values). FIG. 12 is discussed further in conjunction with a discussion of FIG. 13 below.

Figure 13:
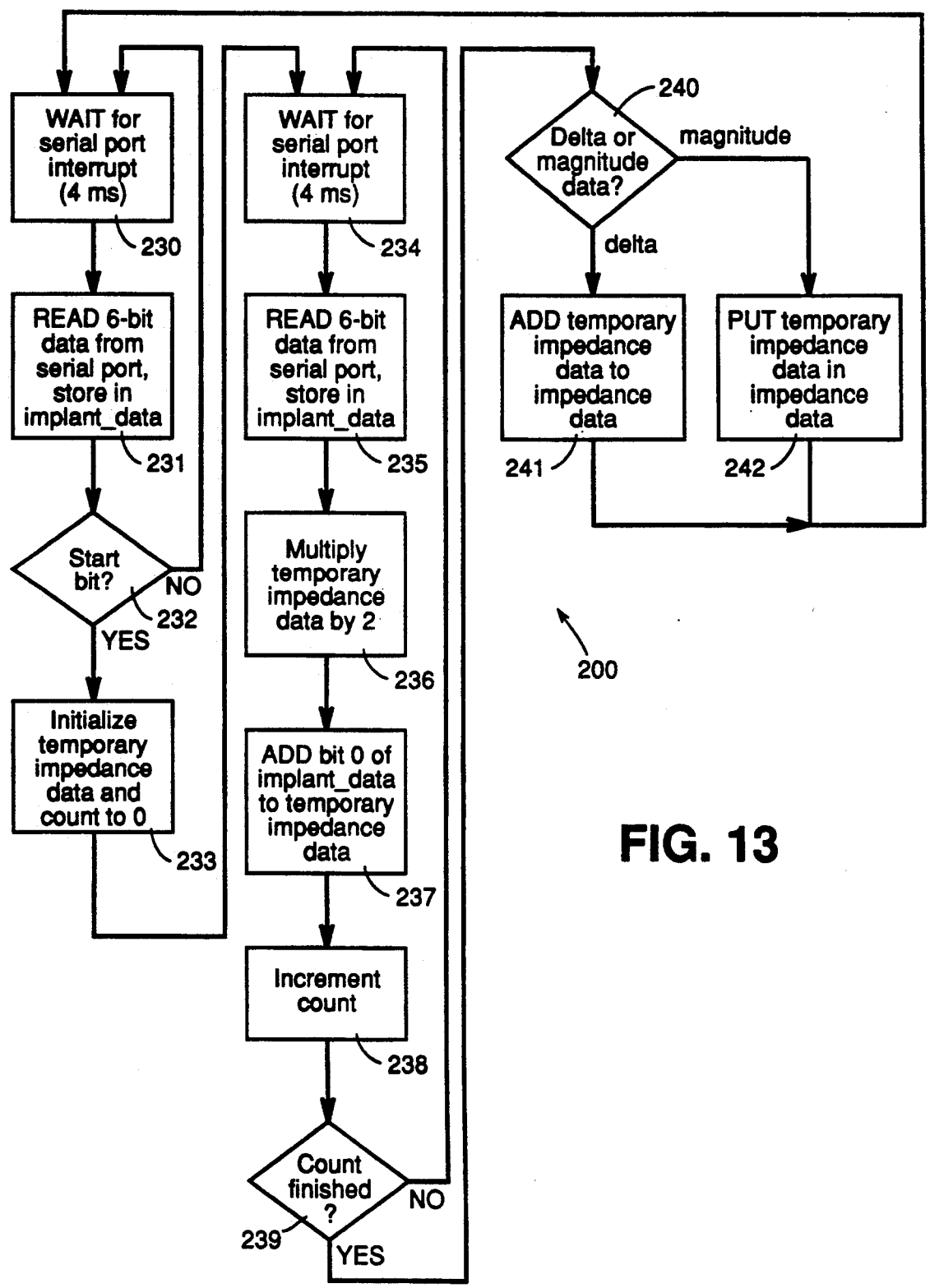
FIG. 13 is a flow chart which describes the operations performed by an external monitoring device computer system for accumulating sensor data and formatting it for display.

FIG. 13 describes the steps performed by the software of general CPU 200 to read combined intracardiac electrogram and impedance data from the serial port 101 and format the impedance information for display. Administrative routines running within the general CPU 200 determine whether the formatting procedure is activated. The RS-232 serial port 101 generates interrupts which activate the general CPU 200. The impedance signal formatting routine, described by FIG. 13, waits for these interrupts in wait-for-serial-port-interrupt block 230. Upon the occurrence of the wakeup, software reads the data in read-6-bit-data-from-serial-port block 231 and stores the data in a memory location called "implant_data". Bit 0 of implant_data holds the serial bit stream of impedance data. Software waits for a "start bit", a "1" value in implant_data. If bit 0 of implant_data is "0", impedance data is not yet available and software returns to block 230, under control by start-bit logic block 232. Otherwise, if the start bit is "1", software initializes the formatting procedure in initialize-temporary-impedance-data-and-count-to-0 block 233. A memory location (accessed by general CPU 200), called "temporary-impedance-data", is used by the formatting routine to accumulate impedance information from the serial bit stream which is sent by the cardiac stimulation device. Temporary-impedance-data is not accessed by other routines which process the impedance data. Block 233 also initializes a memory location, called "count", which stores the count of serial bits which make up the impedance data sample. The number of bits in the serial bit stream is predefined.

The impedance signal formatting routine of FIG. 13 then waits for additional serial port interrupts in wait-for-serial-port-interrupt block 234, which functions in the manner of block 230. Upon the occurrence of the wakeup, software reads the data in read-6-bit-data-from-serial-port block 235 and again stores the data in memory location "implant_data". Software accumulates the serial bit stream of data in multiply-temporary-impedance-data-by-2 block 236 and add-bit-0-of-implant-data-to-temporary-impedance-data block 237. In this manner, software receives bits of impedance data in the order of significance. Increment-count block 238 adds one to the serial bit count.

The total serial bit count of an impedance data element is predetermined. In the preferred embodiment of the invention, eight bits of impedance data should be received. If the accumulation of an impedance data sample is not complete, according to count-finished logic block 239, software returns to block 234 to acquire the next most significant data bit. Otherwise, the impedance data sample has been accumulated. The data may be either in the form of a magnitude or a delta difference between the current sample and the last sample. Administrative software running in the general CPU 200 verifies that the type of data sent by the cardiac stimulation device conforms to that expected by the external monitoring device. Under the control of delta-or-magnitude-data logic block 240, data is stored for access by display routines in a memory location called "impedance-data". Impedance-data is set to the value of temporary-impedance-data without change in put-temporary-impedance-data-in-impedance-data block 242, if the cardiac stimulation device sends magnitude information. Otherwise, if delta information is transmitted, add-temporary-impedance-data-to-impedance-data block 241 accumulates (integrates) the delta values to obtain magnitude information. For either delta or magnitude data, impedance information is in the form of two's complement numbers so that the final magnitude information retains negative and positive sign information. Software then returns to block 230 to wait for the next impedance data sample.

An operator directs the real time sensor data display by keyboard commands to the general CPU 200 via the MSCP 206 (FIG. 11). One of these commands initiates the routine for displaying sensor data, which is illustrated in the flow chart of FIG. 12, in start block 174. This command also specifies whether impedance data or metabolic indicator rate data or both are to be displayed, according to is-data-impedance logic block 175 of FIG. 12. If impedance data is displayed, first-sample-after-start-or-freeze logic block 176 reads a boolean variable that indicates whether the display 208 was previously generating a moving, real time image of impedance data or, alternatively, whether the sensor display was not yet enabled or was placed in a "freeze" condition by an operator command. (The operator of the external monitoring device may invoke a "freeze" command in which the displays for all active real time data channels are stopped and rewritten to the screen with the newest data sample displayed at the far right position on the screen and approximately 20 seconds of real time data frozen on the display 208.) If the current sample is the starting real time sample, software performs an initialization sequence which begins with initialize-history,-load-first-imped-sample-in-history block 177. History is a memory array (in System Memory 210 or Expansion Memory 209 of FIG. 11) for storing a string of impedance and metabolic indicator rate data elements. Block 177 initializes history by setting memory elements to a predetermined value, such as zero, or by setting data pointers to initial locations within the array. Initialize-history,-load-first-imped-sample-in-history block 177 then writes the most recently acquired impedance value to history. In addition, block 177 performs numerous miscellaneous tasks including partitioning the display screen 208 into a graphical real time trace and an edit graphic for entering display commands and parameters, setting vertical and horizontal scale factors for the real time graphic, and drawing the vertical and horizontal scale markers. The impedance signal is scaled to display within a fixed vertical gain ranging from ±3 ohms. Plot-cursor-set-to-far-left block 178 sets the plot cursor memory location to point to the far left side of the real time graphic plot. Then, plot-value-set-to-first-imped-sample block 179 plots the impedance sample by writing a representation of the data value to the display screen via commands from the general CPU 200 to the video controller 203 (of FIG. 11). In first-sample-after-start-or-freeze-is-"NO" block 180, software sets a boolean variable to indicate that a real time display is in process. Finally, sensor display software waits for the next display update cycle by terminating the process in done block 181.

If first-sample-after-start-or-freeze logic block 176 determines that the screen was previously displaying a moving, real time display of impedance data, then plot-impedance-sample block 182 plots the impedance sample by writing a representation of the data value to the display screen 208 via commands from the general CPU 200 to the video controller 203 (of FIG. 11) in a manner similar to that of block 179. Load-impedance-sample-in-history block 183 then writes the newly acquired impedance value to history. Next, software branches to is-data-metabolic-indicator-rate logic block 184 to test for the condition in which both impedance and metabolic indicator rate information are displayed.

Is-data-metabolic-indicator-rate logic block 184 tests for the condition display of metabolic indicator rate information. If not, sensor display software waits for the next display update cycle by terminating the process in done block 196. If metabolic indicator rate information is to be displayed, first-sample-after-start-or-freeze logic block 185 reads the boolean variable indicating whether the screen 208 was previously a real time display or in a disabled or frozen condition. If the current sample is the starting real time sample, software performs an initialization sequence which begins with initialize-history block 186. Block 186 initializes history in the same manner as aforementioned block 177, by setting memory elements to a predetermined value, such as zero, or by setting data pointers to initial locations within the array. In addition, block 186 performs the numerous and miscellaneous display partitioning, scale factor setting and scale marker drawing tasks that are also performed in block 177. Plot-cursor-set-to-initial-X-cursor-position block 187 sets the plot cursor memory location to a predetermined X coordinate position, while plot-cursor-set-to-initial-Y-cursor-position block 188 sets the plot cursor memory location to a predetermined Y coordinate position. Load-metabolic-indicator-rate-in-history block 189 then writes the most recently acquired metabolic indicator rate value to history. In addition to plotting the metabolic indicator rate data to the screen, software (via write-metabolic-indicator-rate-to screen block 190) writes rate information in text to the screen. Block 190 also sets the boolean variable to indicate that a real time display is in process. Finally, sensor display software waits for the next display update cycle by terminating the process in done block 191.

If first-sample-after-start-or-freeze logic block 185 determines that the screen 208 was previously displaying a moving, real time display of impedance data, then plot-metabolic-indicator-rate-sample block 192 plots the rate sample by writing a representation of the data value to the display screen 208 via commands from the general CPU 200 to the video controller 203 (of FIG. 11) in a manner similar to that of blocks 179 and 182. Load-metabolic-indicator-rate-sample-in-history block 193 then writes the newly acquired impedance value to history. Metabolic indicator rate information is displayed both in text form as well as a graphic display using write-metabolic-indicator-rate-to screen block 194. Sensor display software waits for the next display update cycle by terminating the process in done block 195.

From the foregoing discussion, it is apparent that the present invention provides for sensing of physiological signals in an implantable cardiac stimulation device, based upon a measurement of body impedance. The device formats these signals and transmits the formatted signals to an external monitoring device, such as a pacemaker programmer, for display. The ability to visually monitor and distinguish physiological signals corresponding to respiration, cardiac mechanical (pumping) activity and patient motion provides an understanding of cardiovascular hemodynamics and a patient's metabolic demands that was previously available only by means of expensive and invasive electrophysiological studies. The present invention also provides for the simultaneous transmission of combined intracardiac electrogram and physiological signals to quickly and easily set forth the interrelationships between physiological processes such as respiration and cardiac electrical signals, on one hand, or mechanical and electrical cardiac signals, on the other hand. The display of these relationships greatly enhances the diagnostic information available to a physician.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:
1. A cardiac apparatus, comprising:
   means for measuring impedance within a patient's body;
   means for deriving at least one time-varying physiological parameter a function of the measured impedance;
   means for selecting samples of said at least one time-varying physiological parameter;

means for formatting the selected samples into a time sequence of digital samples representing the amplitude of said at least one time-varying physiological parameter;

an external monitoring device;

means for transmitting said formatted samples to said external monitoring device;

means for measuring cardiac electrical signals within the patient's body;

means for selecting samples of said cardiac electrical signals;

means for formatting the selected electrical signals into a time sequence of digital samples representing the amplitude of said cardiac electrical signals; and means for combining said at least one physiological parameter time sequence with said cardiac electrical signal time sequences into a combined sequence of digital samples, wherein said transmitting means transmits said combined sequence of digital samples to said external monitoring device, including:

means for encoding said at least one physiological parameter time sequence into a serial data stream of signal bits, means for encoding said cardiac electrical signal time sequence into a time sequence of multiple-bit digital samples wherein the value of each multiple-bit sample corresponds to an instantaneous amplitude of the cardiac electrical signal, and means for truncating the multiple-bit digital samples by one bit for each of said at least one physiological parameter sequence and replacing each truncated bit with the single bit of said at least one time varying physiological parameter serial data stream of single bits.

2. An apparatus in accordance with claim 1, wherein said combining means includes means for restoring cardiac electrical signal sample bits truncated and replaced by said physiological parameter serial data stream of single bits.

3. An apparatus in accordance with claim 2, wherein said means for restoring truncated and replaced cardiac electrical signal sample bits further comprises:

means for storing the values of bits truncated from preceding time samples of said multiple-bit digital samples, and means for adding the values of said stored truncated bits into subsequent time samples of said multiple-bit digital samples.

4. An apparatus according to claim 3, further including:

two electrodes, coupled to said impedance measuring means, each for interconnection to the patient's body; and wherein:

said impedance measuring means includes:

means for applying a frequency-controlled, time-varying current between said two electrodes, and means for measuring the voltage resulting from the application of said current; and further including:

means for controlling said impedance measuring means, having a mode of operation of setting the timing of, and thereby limiting, the frequency components of said applied current to lie within at least one predetermined subrange of frequencies such that the measured voltage within each subrange of frequencies corresponds to a measurement of at least one said time varying physiological parameter.

5. An apparatus according to claim 4, wherein:

said current applying means, in response to commands from said controlling means, has a mode of operation of generating time varying measuring current in the form of short duration current pulses having pulse durations in a range of approximately 50 to 100 microseconds; and said resultant voltage is provided to said physiological parameter deriving means which derives a respiration signal therefrom.

6. An apparatus in accordance with claim 5, wherein said apparatus further includes a cardiac stimulation pulse generator and means for deriving a cardiac stimulation control signal for controlling said pulse generator, and wherein said deriving means further comprises:

means for analyzing said respiration signal over time to determine a respiratory tidal volume parameter and to detect respiratory signal zero crossings indicative of a respiratory rate parameter;

means for determining a respiratory minute volume parameter as a function of the tidal volume parameter and the respiratory rate parameter;

means for ascertaining an indication of the time average of said respiratory minute volume parameter over both a short time period and a long time period to determine a short-term average respiration signal and a long-term average respiration signal, respectively; and means for determining a metabolic demand pacing rate as a function of the difference between said short-term average respiration signal and said long-term average respiration signal.

7. An apparatus according to claim 6, wherein:

said physiological parameter deriving means has a mode of operation wherein it derives at least one physiological parameter which is selected from the group of parameters which includes:

the respiration signal,
the respiratory tidal volume parameter,
the respiration rate parameter,
the respiratory minute volume parameter,
the short-term average respiration signal, and
the long-term average respiration signal;

said formatting means formats said at least one physiological parameter;

said transmitting means transmits said at least one physiological parameter; and said external monitoring device receives and displays said at least one physiological parameter.

8. An apparatus according to claim 5, wherein:

said physiological parameter deriving means derives at least two physiological parameters;

said current applying means, in response to commands from said controlling means, has a mode of operation wherein it generates a third time varying measuring current in the form of short duration current pulses having pulse durations shorter than approximately 70 nanoseconds, and said respective third voltage is provided to said physiological parameter deriving means which derives a patient motion signal therefrom.

9. An apparatus according to claim 5 wherein:

said current applying means, in response to commands from said controlling means, has a mode of operation wherein it generates the time varying measuring current pulses having pulse durations longer than 300 nanoseconds; and said resultant voltage measured by said measuring means is provided to said physiological parameter deriving means, which derives a cardiac hemodynamic signal therefrom.

10. An apparatus according to claim 5 wherein:

said physiological parameter deriving means derives at least two physiological parameters;

said current applying means, in response to commands from said controlling means, has a mode of operation wherein it generates a second time varying measuring current in the form of short duration current pulses having pulse durations shorter than approximately 70 nanoseconds; and said measuring means measures a second voltage that is provided to said physiological parameter deriving means, which derives a patient motion signal therefrom.

11. An apparatus according to claim 4, wherein:

said physiological parameter deriving means derives at least two physiological parameters;

said current applying means, in response to commands from said controlling means, has a mode of operation of generating a second time-varying measuring current in the form of short duration current pulses having pulse durations longer than approximately 300 nanoseconds; and said respective second voltage is provided to said physiological parameter deriving means which derives a cardiac hemodynamic signal therefrom.

12. An apparatus according to claim 11, wherein:

said current applying means in response to commands from said controlling means, has a mode of operation wherein it generates the time varying measuring current in the form of short duration current pulses having pulse durations shorter than approximately 70 nanoseconds; and the voltage measured by said measuring means is provided to said physiological parameter deriving means, which derives a patient motion signal therefrom.

13. An apparatus according to claim 11 further including;

two electrodes, coupled to said impedance measuring means, each for interconnection to the patient's body, for sensing signals and for delivering stimulation pulses; and wherein:

said impedance measuring means further includes:
means for applying a frequency controlled, time varying current between said two electrodes, and
means for measuring a voltage in response to the application of the measuring current; and further including:

means for controlling said measuring means, operable to set the timing of, and to thereby limit, the frequency components of the applied time varying current to lie within at least one predetermined subrange of frequencies such that the measured voltage within each subrange of frequencies corresponds to a measurement of said time varying physiological parameter; and means for deriving said at least one time varying physiological parameter from the measured voltage corresponding to the predetermined subrange of frequencies.

14. A method for monitoring at least one time varying physiological parameter sensed by a device implanted in the patient, said device having:

means for monitoring a physiological signal, and
means for transmitting a representation of the physiological signal to an external monitoring device for display;

said method comprising:

measuring an impedance within the body of the patient;

deriving at least one time varying physiological parameter as a function of the measured impedance;

selecting samples of said at least one time varying physiological parameter;

formatting said samples of said parameter into a digital time sequence of samples representing the amplitude of said parameter;

sensing cardiac electrical signals;

sampling and formatting said cardiac electrical signals to generate a time sequence of digital samples representing the amplitude of said cardiac electrical signals; and combining said at least one physiological parameter time sequence with said cardiac electrical signal time sequence into a combined sequence of digital samples and transmitting said combined sequence of digital samples to said external monitor, by:
encoding each of said at least one physiological parameter time sequence samples into a serial data stream of single bits,
encoding said cardiac electrical signal time sequence into a time sequence of multiple-bit samples wherein the value of each multiple-bit sample corresponds to an instantaneous amplitude of the cardiac electrical signal, and
truncating the multiple-bit digital samples by one bit for each of said at least one physiological parameter sequence and replacing each truncated bit with the single bit of said at least one time varying, physiological parameter serial data stream of single bits.

15. A method in accordance with claim 14, wherein said combining step includes the sub-step of restoring cardiac electrical signal sample bits truncated and replaced by said physiological parameter serial data stream of bits.

16. A method in accordance with claim 15, wherein said sub-step of restoring truncated and replaced cardiac electrical signal sample bits further comprises the sub-steps of:

storing the values of bits truncated from preceding time samples of said multiple-bit digital samples, and adding the values of said stored truncated bits into subsequent time samples of said multiple-digital samples.

17. A method according to claim 16, said implanted device having at least two electrodes for sensing signals and delivering stimulation pulses, and wherein:

said impedance measuring step includes the sub-steps of:
applying a frequency controlled, time varying current between two of said at least two electrodes, and
measuring the voltage responding to said application of said measuring current; and wherein said method further comprises:

controlling said impedance measuring step to set the timing of, and to thereby limit, the frequency components of the applied time varying current to lie within at least one predetermined subrange of frequencies such that the measured voltage within each subrange of frequencies corresponds to a measurement of said time varying physiological parameter; and deriving said at least one time varying physiological parameter from the measured voltage corresponding to the predetermined subrange of frequencies.

18. A method according to claim 14, said implanted device having at least two electrodes for sensing signals and delivering stimulation pulses, and wherein:

said impedance measuring step includes the sub-steps of:

applying a frequency controlled, time varying current between two of said at least two electrodes, and measuring a voltage responding to said application of said measuring current; and wherein said method further comprises:

controlling said impedance measuring step to set the timing of, and to thereby limit, the frequency components of the applied time varying current to lie within at least one predetermined subrange of frequencies such that the measured voltage within each subrange of frequencies corresponds to a measurement of said time varying physiological parameter; and deriving said at least one time varying physiological parameter from the measured voltage corresponding to the predetermined subrange of frequencies.

* * * * *